US012636008B2

(12) United States Patent
Jaworek et al.

(10) Patent No.: US 12,636,008 B2

(45) Date of Patent: May 26, 2026

(54) CLAMP FORCE SENSOR FOR SURGICAL STAPLER

(71) Applicant: Cilag GmbH International, Zug (CH)

(72) Inventors: Gary S. Jaworek, Cincinnati, OH (US); Christopher J. Schall, Mason, OH (US); Mark J. Bookbinder, Blue Ash, OH (US); Bingshi Wang, Mason, OH (US); Luling Wang, Mason, OH (US); Laura S. Downing, Cincinnati, OH (US); John P. May, Mason, OH (US); Shannon L Jones, Cincinnati, OH (US); Nicholas Fanelli, Morrow, OH (US); Gregory G. Scott, Cincinnati, OH (US); Bradley A. Arnold, Mason, OH (US); Nicholas W. Seipelt, Milford, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/500,305

(22) Filed: Nov. 2, 2023

(65) Prior Publication Data

US 2025/0143696 A1 May 8, 2025

(51) Int. Cl.
*A61B 17/072* (2006.01)
*A61B 17/00* (2006.01)
*A61B 90/00* (2016.01)

(52) U.S. Cl.
CPC .. *A61B 17/072* (2013.01); *A61B 2017/00221* (2013.01); *A61B 2017/00734* (2013.01); *A61B 2017/07264* (2013.01); *A61B 2017/07271* (2013.01); *A61B 2090/064* (2016.02); *A61B 2090/0811* (2016.02);
(Continued)

(58) Field of Classification Search
CPC ............... A61B 17/068; A61B 17/072; A61B 2017/00017
See application file for complete search history.

(56) References Cited

U.S. PATENT DOCUMENTS

| | | | |
|---|---|---|---|
| 7,334,717 B2 * | 2/2008 | Rethy | A61B 17/105 |
| | | | 227/175.3 |
| 7,784,663 B2 | 8/2010 | Shelton, IV | |

(Continued)

OTHER PUBLICATIONS

U.S. Appl. No. 18/500,297, filed Nov. 2, 2023, by Schings, entitled: "Strain and Compression Force Measurement Features for Surgical Stapler.".

(Continued)

*Primary Examiner* — Gloria R Weeks

(74) *Attorney, Agent, or Firm* — FBT GIBBONS LLP

(57) ABSTRACT

An apparatus includes a first and second elongate member that can releasably couple together to in order to cooperate to clamp and staple tissue, a latch member that can latch the first and second elongate member to clamp tissue, a firing assembly that can sever and staple clamped tissue, and a clamp force measuring assembly. The clamp force measuring assembly can measure a parameter associated with a clamping force imparted on the first and second stapling surfaces while clamping tissue, and process and communicate the measured parameter to be compared with a predetermined limit associated with successful staple formation.

15 Claims, 32 Drawing Sheets

(52) U.S. Cl.
CPC ................. *A61B 2560/0443* (2013.01); *A61B 2562/0261* (2013.01); *A61B 2562/04* (2013.01)

(56) References Cited

U.S. PATENT DOCUMENTS

| | | | | |
|---|---|---|---|---|
| 8,851,354 | B2 * | 10/2014 | Swensgard | A61B 17/105 227/176.1 |
| 9,724,094 | B2 * | 8/2017 | Baber | H02H 3/207 |
| 10,052,044 | B2 * | 8/2018 | Shelton, IV | A61B 5/0538 |
| 10,357,247 | B2 * | 7/2019 | Shelton, IV | A61B 17/32 |
| 10,405,859 | B2 * | 9/2019 | Harris | G16H 20/40 |
| 10,631,866 | B2 | 4/2020 | Laurent et al. | |
| 10,667,818 | B2 | 6/2020 | McLain et al. | |
| 10,687,819 | B2 | 6/2020 | Stokes et al. | |
| 10,874,398 | B2 | 12/2020 | Baxter, III et al. | |
| 10,898,187 | B2 | 1/2021 | Deck et al. | |
| 10,898,197 | B2 | 1/2021 | Baxter, III et al. | |
| 10,905,419 | B2 * | 2/2021 | Schings | A61B 17/07207 |
| 10,932,781 | B2 | 3/2021 | Jones et al. | |
| 11,033,266 | B2 | 6/2021 | Jones et al. | |
| 11,045,193 | B2 | 6/2021 | Schings et al. | |
| 11,071,545 | B2 * | 7/2021 | Baber | A61B 17/00 |
| 11,109,866 | B2 * | 9/2021 | Shelton, IV | H01Q 1/22 |
| 11,219,454 | B2 | 1/2022 | Schings et al. | |
| 11,224,425 | B2 | 1/2022 | Schings | |
| 11,229,433 | B2 | 1/2022 | Schings et al. | |
| 11,278,285 | B2 | 3/2022 | Deck et al. | |
| 11,284,894 | B2 | 3/2022 | Park | |
| 11,399,827 | B2 | 8/2022 | Schings | |
| 11,937,812 | B2 | 3/2024 | Schings et al. | |
| 2005/0131390 | A1 | 6/2005 | Heinrich et al. | |
| 2006/0273135 | A1 * | 12/2006 | Beetel | A61B 17/128 227/175.1 |
| 2011/0155781 | A1 * | 6/2011 | Swensgard | A61B 17/07207 227/176.1 |
| 2017/0296185 | A1 * | 10/2017 | Swensgard | A61B 17/068 |
| 2021/0361376 | A1 * | 11/2021 | Eschbach | G16H 20/40 |
| 2022/0008071 | A1 | 1/2022 | Rose et al. | |
| 2022/0142641 | A1 | 5/2022 | Wang | |
| 2022/0406452 | A1 | 12/2022 | Shelton, IV | |
| 2023/0123673 | A1 | 4/2023 | Gonenc et al. | |
| 2023/0329704 | A1 | 10/2023 | Hess et al. | |
| 2025/0041000 | A1 * | 2/2025 | Shelton, IV | G16H 20/40 |

OTHER PUBLICATIONS

Design U.S. Appl. No. 29/842,580, filed Jun. 14, 2022, by Schings et al., entitled: "Staple Cartridge for a Linear Surgical Stapler.".
Design U.S. Appl. No. 29/842,581, filed Jun. 14, 2022, by Deck et al., entitled: "Linear Surgical Stapler.".
European Extended Search Report and Written Opinion dated Dec. 10, 2024, for Application No. 24209381.3, 10 pages.
European Extended Search Report and Written Opinion dated Feb. 17, 2025, for Application No. 24209384.7, 8 pages.

\* cited by examiner

SURGEON'S CONSOLE

SURGEON'S CONSOLE

1200

CLAMP FORCE SENSOR FOR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to releasably couple together and pivot relative to one another to clamp tissue positioned between the two distal jaws when the clamp lever is closed. A firing assembly of the stapler is configured to be actuated to cut the clamped layers and simultaneously drive staples through the tissue on either side of the cut line. After the stapler is fired, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
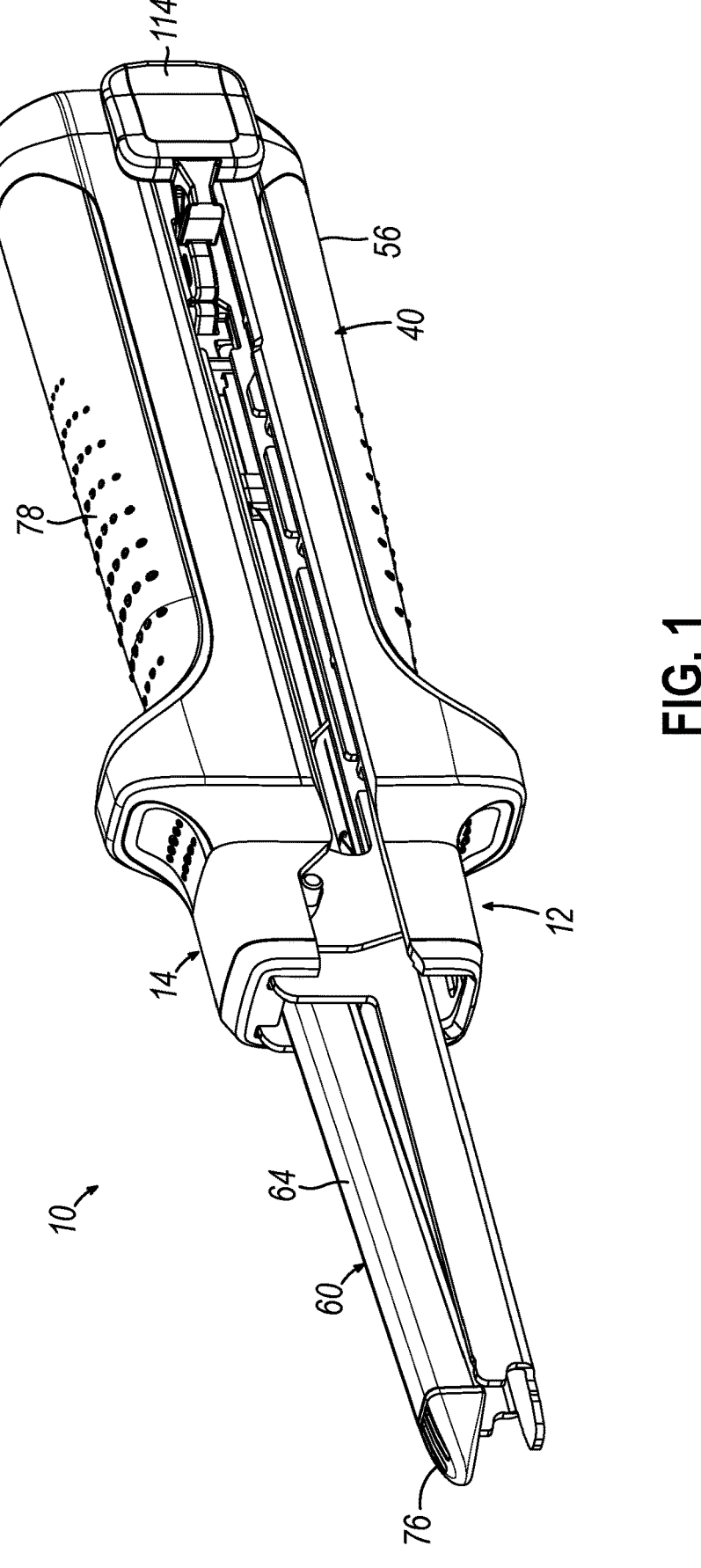
FIG. 1 depicts a perspective view of an illustrative linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for illustrative description purposes only and are not intended to be limiting or absolute. In that regard, it will be understood that surgical instruments such as those disclosed herein may be used in a variety of orientations and positions not limited to those shown and described herein.

Furthermore, the terms "about" and "approximately" as used herein in connection with any numerical values or ranges indicate a suitable dimensional tolerance that allows the referenced feature(s) to function for its intended purpose as described herein.

I. Illustrative Linear Surgical Staplers

A. Overview of Linear Surgical Stapler

Figure 2:
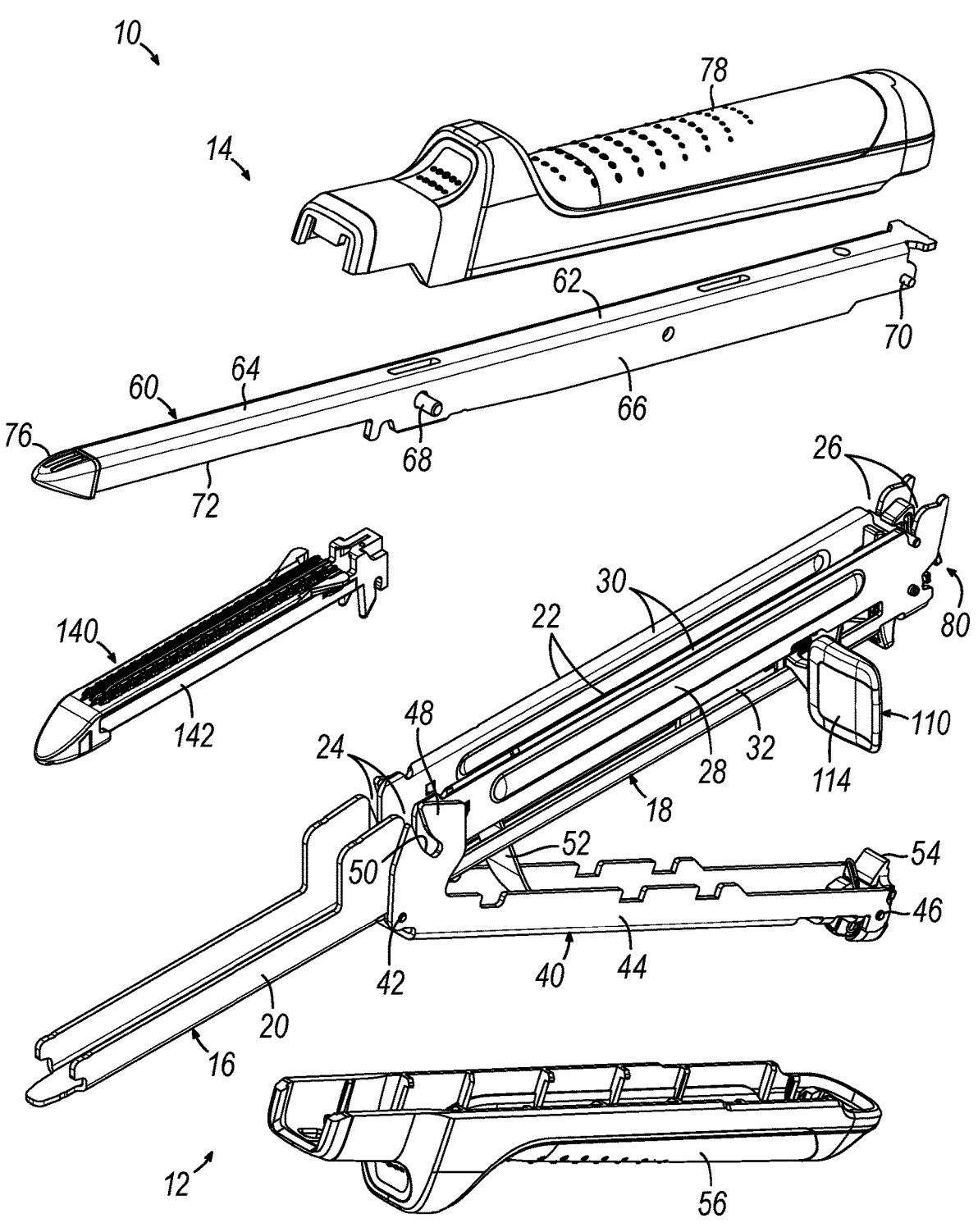
FIG. 2 depicts an exploded perspective view of the linear surgical stapler of FIG. 1, additionally showing a staple cartridge.

FIGS. 1-2 show an illustrative linear surgical stapler (10) (also referred to as a "linear cutter") suitable for use in a variety of cutting and stapling procedures, such as a gastro-intestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) includes a first elongate member and/or body in the form of an elongate cartridge channel (16) having a proximal frame portion (18) and a distal jaw portion (20). Proximal frame portion (18) slidably retains a firing assembly (110) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (110) between proximal and distal positions. Firing assembly (110) is described in greater detail below in connection with FIG. 8.

Figure 4:
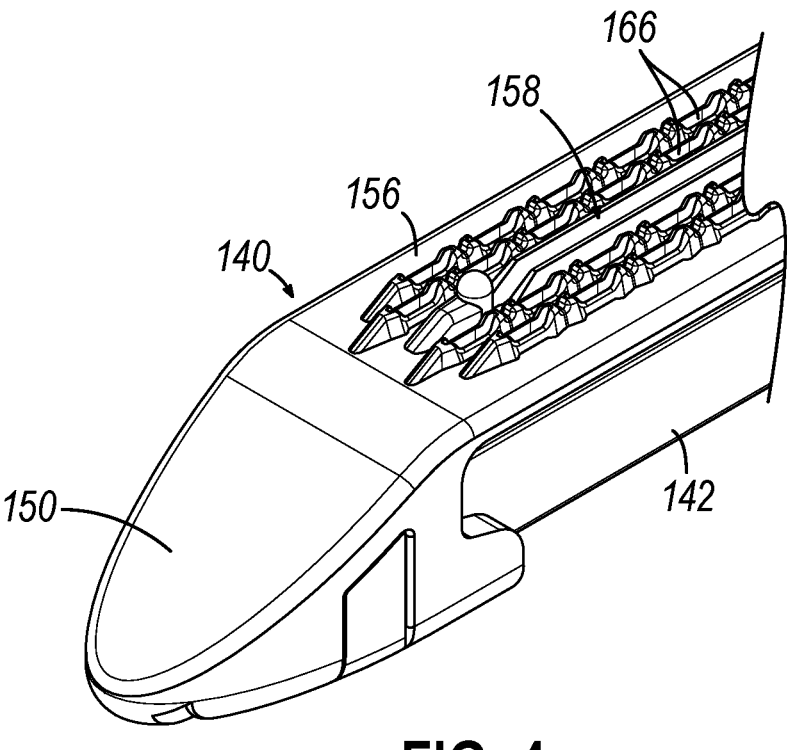
FIG. 4 depicts a perspective view of a distal end portion of the staple cartridge of FIG. 2.

Distal jaw portion (20) of cartridge channel (16) is configured to releasably receive a staple cartridge (140) (or "reload"). As shown in FIG. 4, staple cartridge (140) includes a cartridge body (142) having an upper side that defines a first stapling surface in the form of a deck (156) having a plurality of staple openings (166) that house a plurality of staples and corresponding staple drivers.

Cartridge half (12) further includes a clamp member in the form of a clamp lever (40) (also referred to as a "clamp arm" or "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 9A:
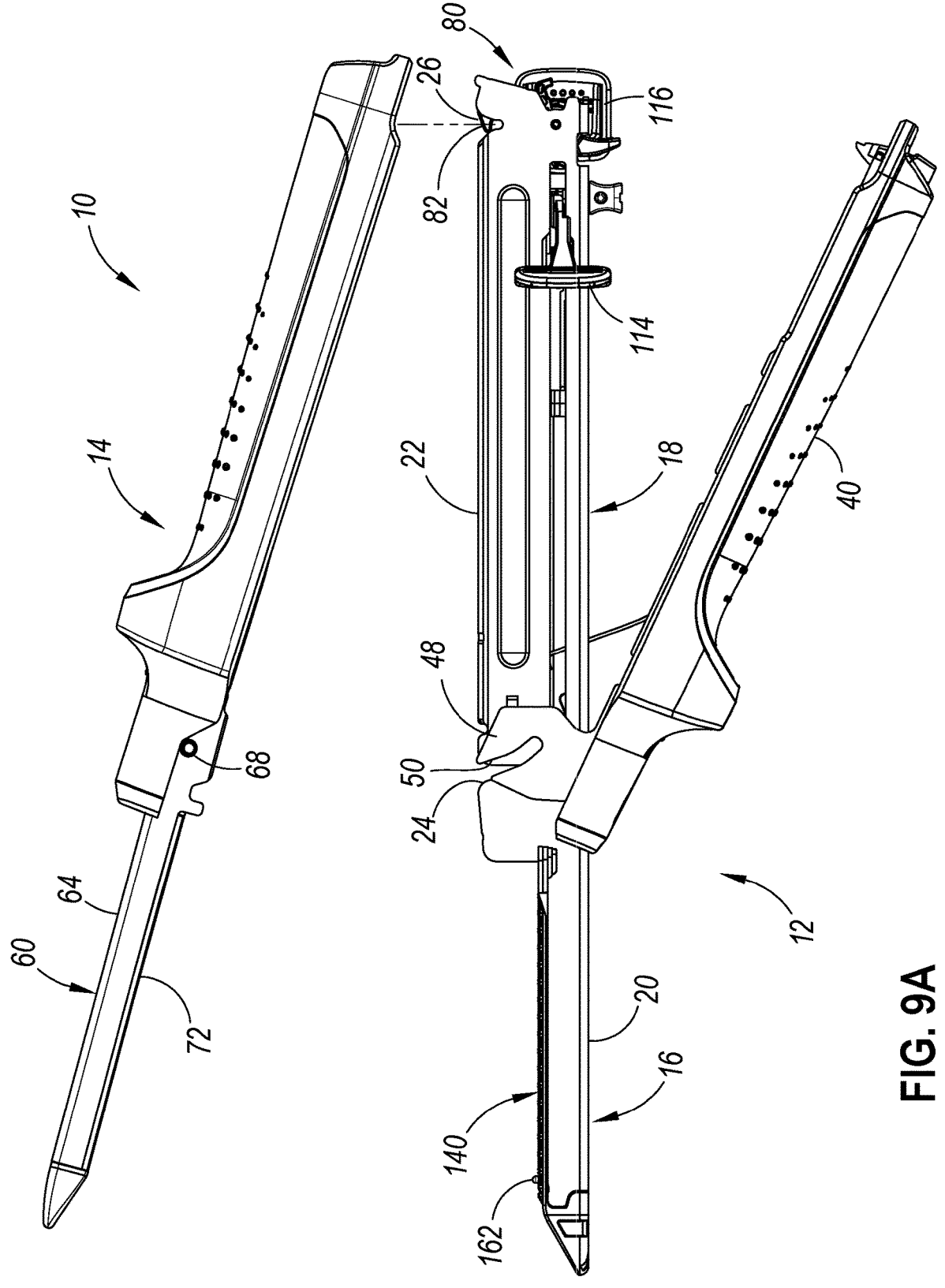
FIG. 9A depicts a side elevational view of the linear surgical stapler of FIG. 1, showing the stapler halves separated from one another with the clamp lever in the open position.
Figure 9B:
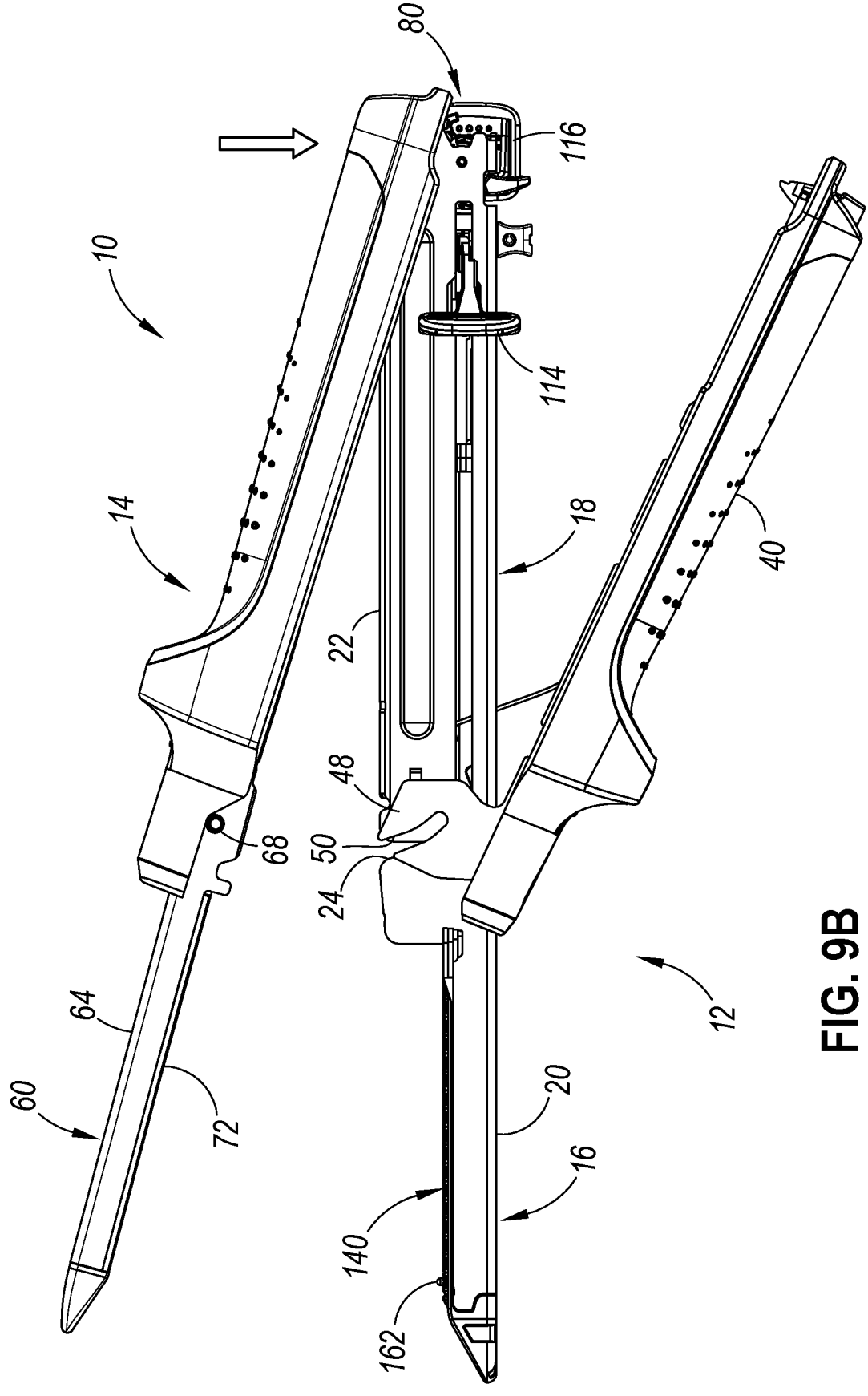
FIG. 9B depicts a side elevational view of the linear surgical stapler of FIG. 1, showing proximal ends of the stapler halves coupled together while the clamp lever is in the open position to provide the stapler in a "hang-open" state.
Figure 9C:
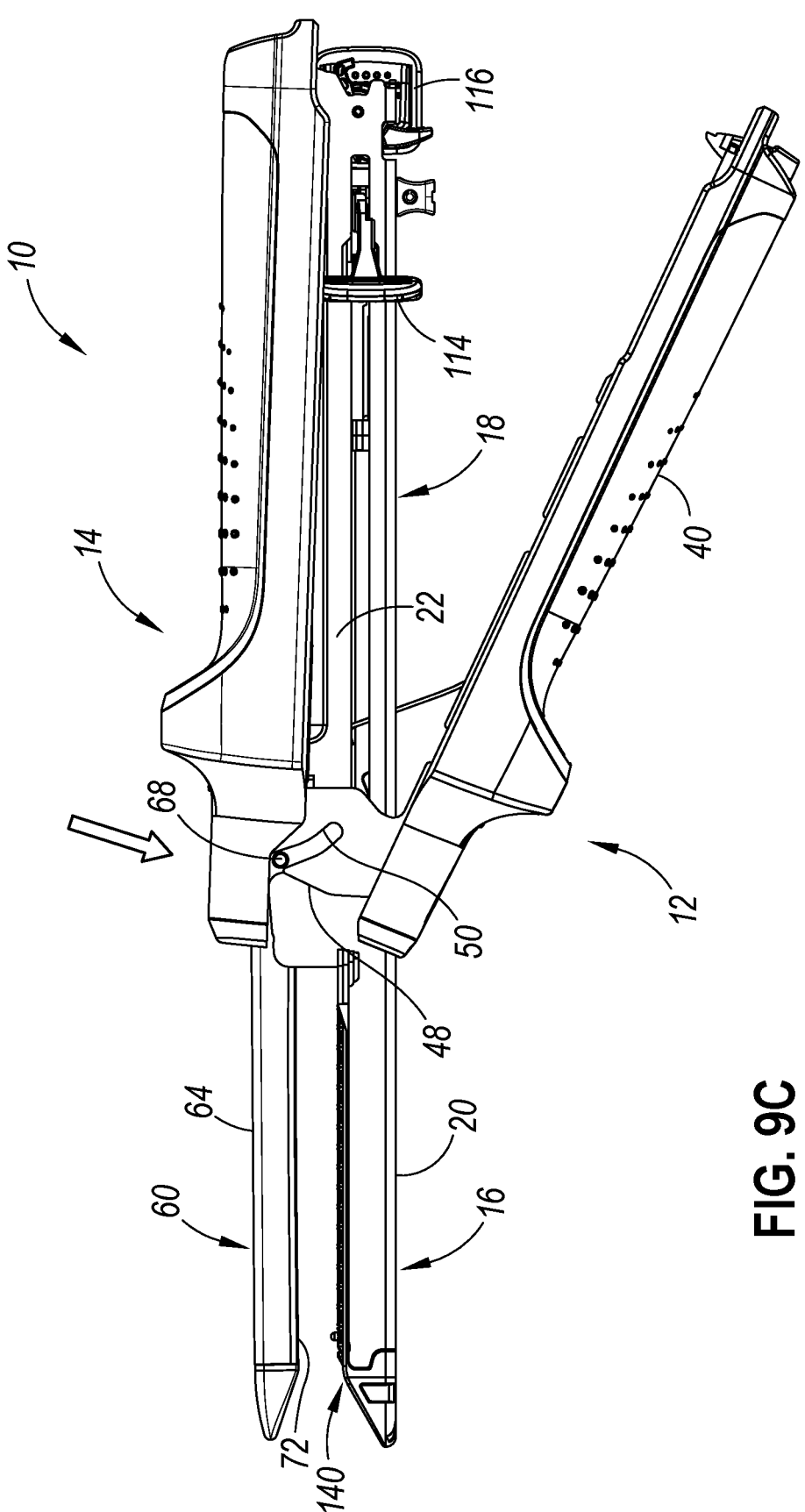
FIG. 9C depicts a side elevational view of the linear surgical stapler of FIG. 1, showing distal portions of the stapler halves having been approximated so that a distal pin of the anvil half is received by clamp lever jaws of the cartridge half.
Figure 9D:
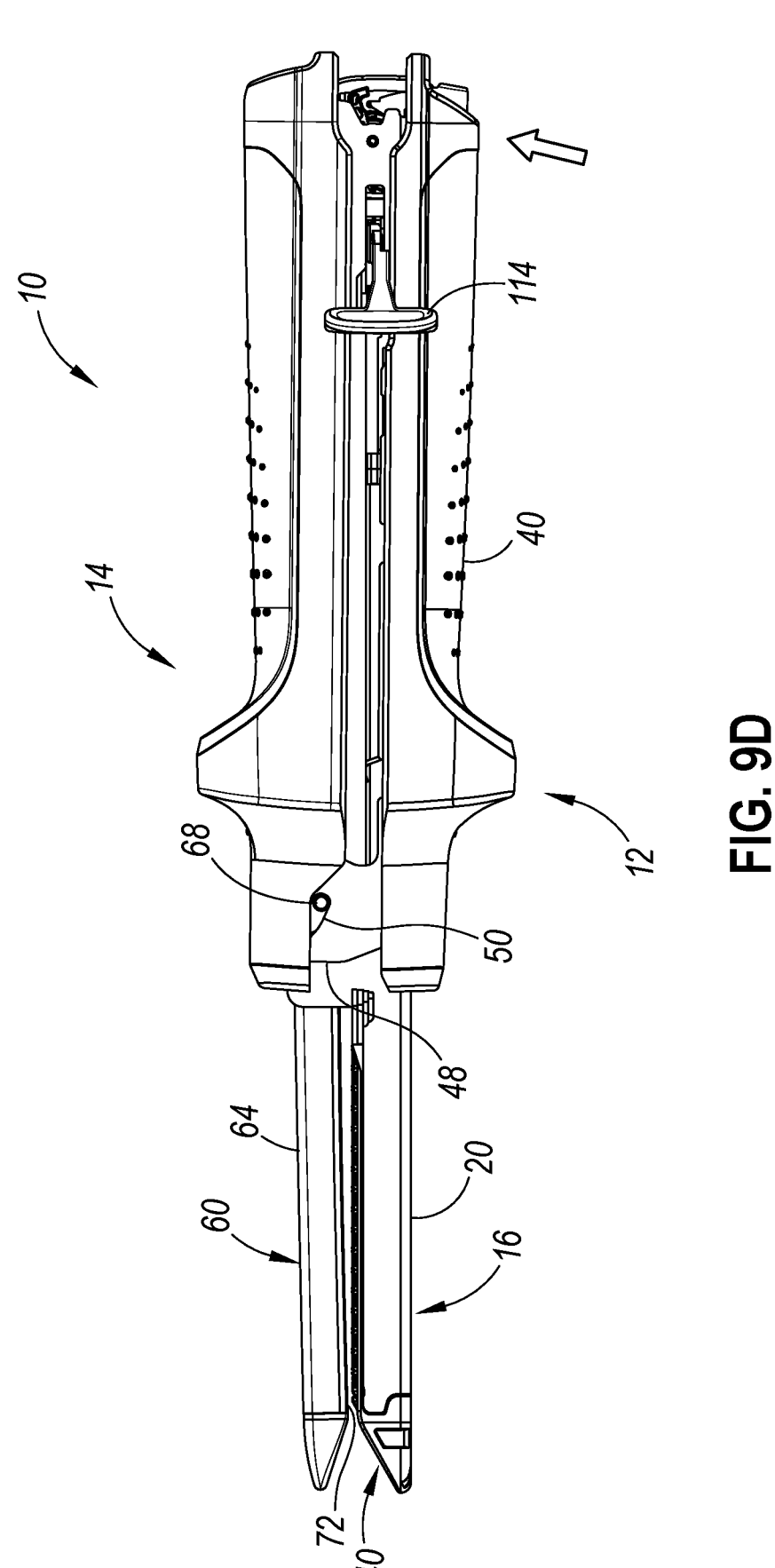
FIG. 9D depicts a side elevational view of the linear surgical stapler of FIG. 1, showing closure of the clamp lever to fully clamp the stapler halves together.
Figure 9E:
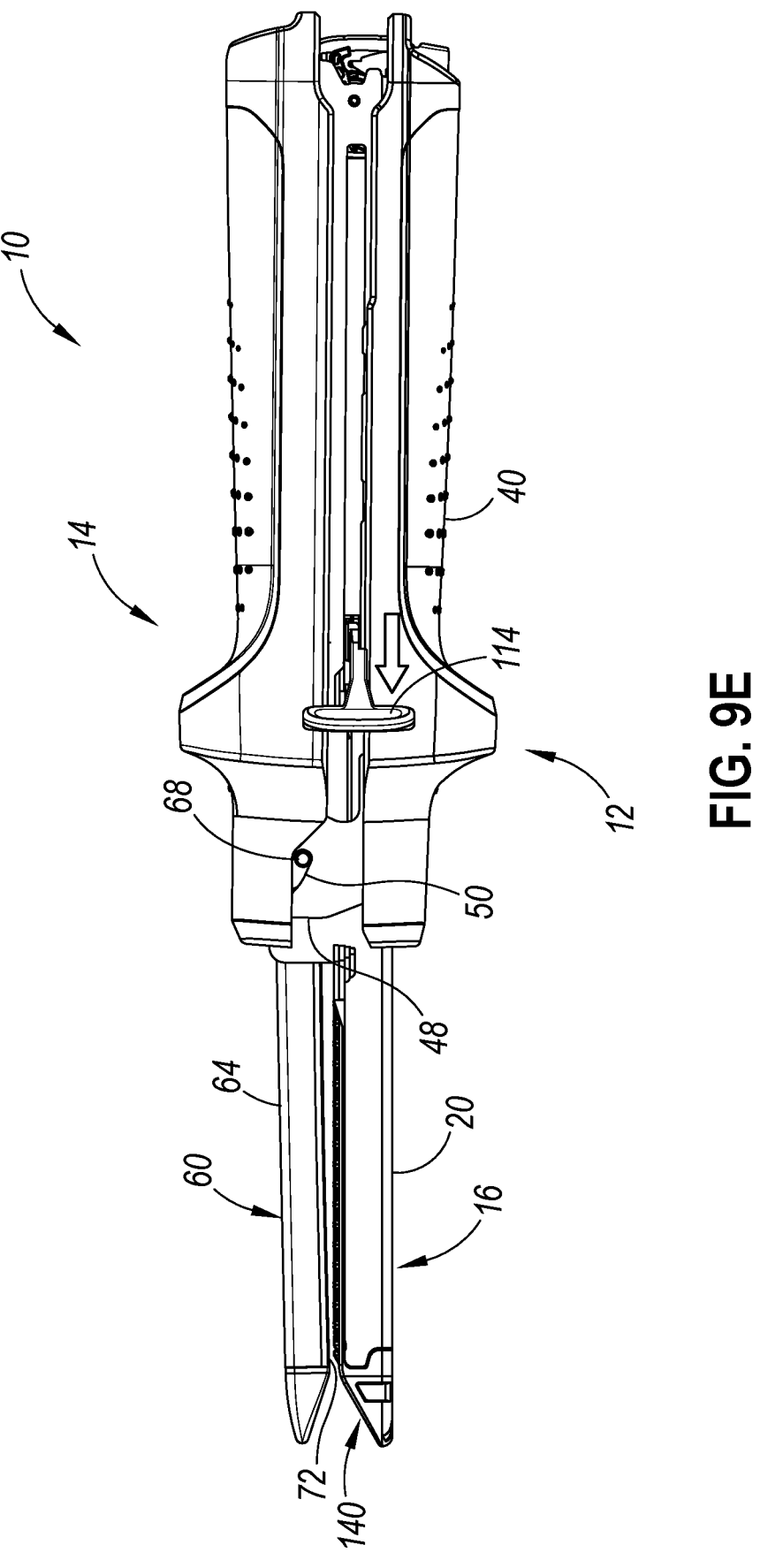
FIG. 9E depicts a side elevational view of the linear surgical stapler of FIG. 1, showing distal actuation of the firing assembly while the stapler halves are in the fully clamped state.

Clamp lever (40) is operable to pivot relative to cartridge channel (16) between an open position in which proximal end (46) of lever arm (44) is spaced from cartridge channel frame portion (18) as shown in FIGS. 9A-9C described below, and a closed position in which proximal end (46) confronts cartridge channel frame portion (18) as shown in FIG. 9D described below. Actuation of clamp lever (40)

from the open position to the closed position operates to capture the opposed lateral ends of latch pin (68) within clamp lever jaw slots (50), and thereby clamp anvil half (14) against cartridge half (12), as shown and described below in connection with FIGS. 9C-9D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a leaf spring (52) biases lever arm (44) toward the open position. Accordingly, leaf spring (52) promotes disengagement of clamp lever jaws (48) from anvil half latch pin (68) upon initial advancement of clamp lever (40) from the closed position toward the open position.

As best shown in FIG. 2, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired. Clamp lever latch member (54) may be further configured in accordance with the teachings of U.S. Pat. No. 11,278,285, entitled "Clamping Assembly for Linear Surgical Stapler," issued Mar. 22, 2022, the disclosure of which is incorporated by reference herein.

Anvil half (14) of linear surgical stapler (10) includes a second elongate member and/or body in the form of an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil half pins (68, 70) are configured to facilitate coupling of anvil half (14) with cartridge half (12), as described below.

Figure 3:
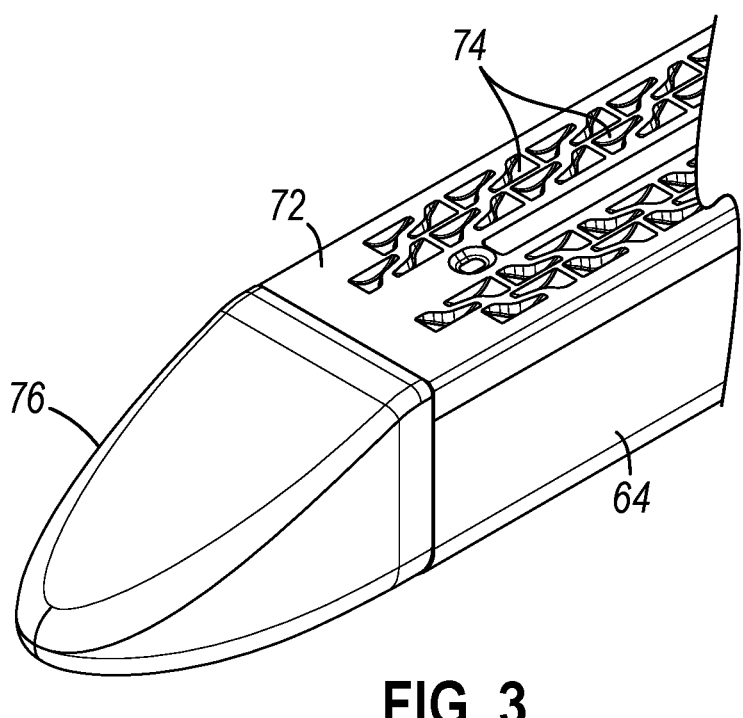
FIG. 3 depicts a perspective view of a distal end portion of the anvil half of the linear surgical stapler of FIG. 1.

As shown in FIGS. 2 and 3, distal jaw portion (64) of anvil half (14) supports an anvil plate (72) that defines a second stapling surface in the form of an anvil surface having a plurality of staple forming pockets (74) configured to deform legs of staples ejected by staple cartridge (140) when stapler (10) is fired. Staple forming pockets (74) of the present example may be formed via a coining process and are configured to form each staple of staple cartridge (140) with a three-dimensional shape in which the legs of each formed staple are laterally offset from one another so as to provide the formed staple with a non-planar shape, for example as disclosed in U.S. Pat. No. 11,229,433, entitled "Linear Surgical Stapler," issued Jan. 25, 2022, the disclosure of which is incorporated by reference herein. Anvil channel (60), anvil plate (72), and staple forming pockets (74) may be formed in one or more of the manners disclosed in U.S. Pat. Nos. 11,229,433; 11,045,193, entitled "Anvil Assembly for Linear Surgical Stapler," issued Jun. 29, 2021; and/or U.S. Pub. No. 2022/0142641, entitled "System and Method for Forming Pockets in Anvil of Surgical Stapler," published May 12, 2022, issued as U.S. Pat. No. 12,016,555 on Jun. 25, 2024, the disclosures of which are incorporated by reference herein. For instance, distal jaw portion (64) of anvil half (14) may be pre-formed with a curvature along its length that accommodates deflection of distal jaw portion (64) and anvil plate (72) when stapler halves (12, 14) are clamped together by clamp lever (40). Distal jaw portion (64) of anvil half (14) additionally supports a tapered distal tip member (76). In some versions, distal tip member (76) may be selectively extendable relative to distal jaw portion (64) in accordance with the teachings of U.S. Pat. No. 11,033,266, entitled "Decoupling Mechanism for Linear Surgical Stapler, issued Jun. 15, 2021, the disclosure of which is incorporated by reference herein.

As shown in FIG. 2, linear surgical stapler (10) further includes a pair of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) via interaction between pins (68, 70) and one or more tabs, ribs, or other structures that are disposed within an interior of anvil shroud (78) and include an opening, slot, keyhole, or other feature configured to receive a respective one of pins (68, 70). By way of example only, shrouds (56, 78) may be affixed using one or more of the teachings of U.S. Pat. No. 11,278,285, incorporated by reference above. In other versions, shrouds (56, 78) may be coupled with clamp lever (40) and anvil channel (60) in a variety of other suitable manners readily apparent to those of ordinary skill in the art in view of the teachings herein.

As shown best in FIGS. 2 and 5-7, a proximal end of cartridge half (12) includes a retaining assembly (80) configured to releasably retain portions of anvil half (14) and firing assembly (110). Retaining assembly (80) of the present example includes a first movable retaining member in the form of an anvil latch member (82) and a second movable retaining member in the form of a detent member (84). Anvil latch member (82) and detent member (84) are rotatably coupled with a proximal end of cartridge channel (16) via a laterally extending pin (85) arranged proximally of firing slots (32), and members (82, 84) are resiliently biased in opposite rotational directions by a resilient member in the form of a torsion spring (86) positioned between members (82, 84).

Anvil latch member (82) includes a central body (88), a latch finger (90) extending upwardly from central body (88), and a release button (92) extending downwardly from central body (88) though a base wall of proximal frame portion (18) of cartridge channel (16). An upper end of latch finger (90) tapers distally and is configured to releasably capture proximal anvil pin (70) of anvil half (14) with an angled latching surface (94) that overlies proximal anvil pin (70) once captured. Anvil latch member (82) further includes a pin ejection feature in the form of an angled projection (96) extending distally from a base portion of latch finger (90) and which defines an ejection cam ramp (98) that faces proximally toward latch finger (90).

Detent member (84) of proximal retaining assembly (80) includes a generally cylindrical central body (100), a distal finger (102) extending distally from central body (100), and a proximal hook (104) extending proximally from central body (100). Distal finger (102) is configured to releasably engage a proximal end of firing assembly (110) and thereby retain firing assembly (110) in a proximal home position. Proximal hook (104) is configured to overlie and capture an upper tip of clamp lever latch member (54) when clamp lever (40) is fully closed and firing assembly (110) is translated distally from its proximal home position, thereby preventing clamp lever (40) from opening during a firing stroke, for example as described in greater detail in U.S. Pat. No. 11,278,285, incorporated by reference above.

In use, with stapler halves (12, 14) coupled together at their proximal ends such that proximal anvil pin (70) is retained by anvil latch member (82), and with clamp lever (40) in the open position, distal actuation of lower release button (92) causes anvil latch member (82) to rotate about pin (85) such that ejection cam ramp (98) advances proximally to drive proximal anvil pin (70) upwardly out of proximal tapered notches (26) of cartridge channel (16). Cartridge half (12) of the present version further includes a stationary finger grip projection (106) that extends downwardly from a base wall of proximal frame portion (18) of cartridge channel (16) at a location distal to lower release button (92), and is configured to facilitate actuation of release button (92). In particular, a user may apply his or her thumb to a proximal side of release button (92) and one or more fingers to a distal side of finger grip projection (106), and then squeeze release button (92) distally toward stationary finger grip projection (106) to rotate latch finger (90) out of engagement with proximal anvil pin (70) and eject pin (70) upwardly from cartridge channel (16) with ejection cam ramp (98).

Retaining assembly (80) and related components of cartridge half (12) may be further configured and operable in accordance with one or more teachings of U.S. Pat. No. 10,898,187, entitled "Firing System for Linear Surgical Stapler," issued Jan. 26, 2021, the disclosure of which is incorporated by reference herein; and/or U.S. Pat. No. 11,033,266, incorporated by reference above.

Figure 8:
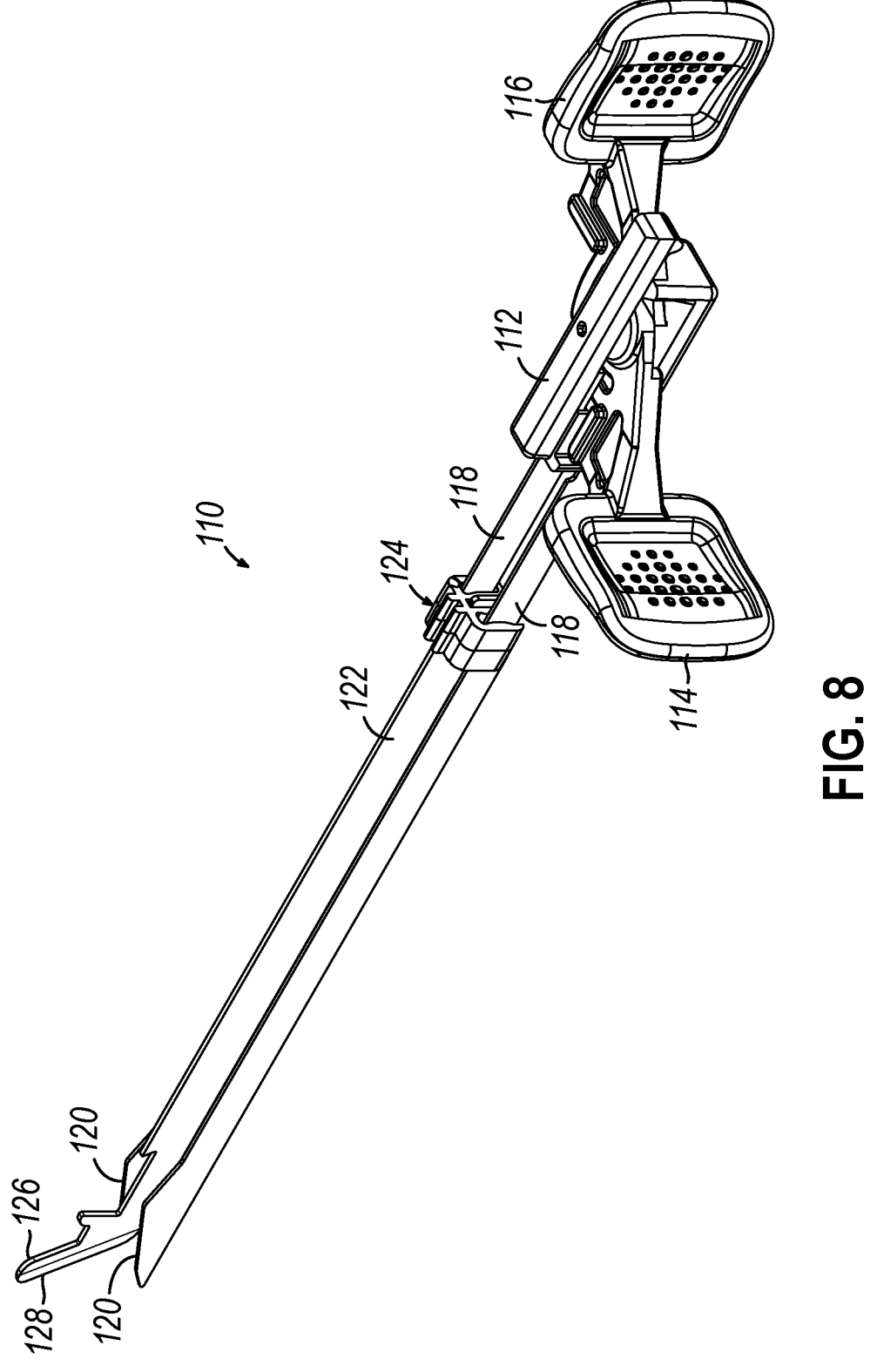
FIG. 8 depicts a perspective view of the firing assembly of FIG. 5.

As shown in FIG. 8, firing assembly (110) of cartridge half (12) includes a slide block (112), a pair of actuators (114, 116) (or "firing knobs") pivotably coupled to slide block (112), and a set of elongate beams (118, 122) extending distally from slide block (112). A pair of side beams (118) are coupled at their proximal ends to a distal end of slide block (112) and terminate distally in a pair of cam ramps (120). Cam ramps (120) are configured to engage the undersides of staple drivers (not shown) housed within staple cartridge (140) and actuate staple drivers (not shown) upwardly to thereby drive (or "fire") staples from cartridge (140) into tissue clamped between staple cartridge (140) and anvil plate (72). A center beam (122) is coupled with side beams (118) via a bridge member (124) (or "knife block") spaced distally from slide block (112). Center beam (122) terminates distally in a distally angled knife member (126) having a distal cutting edge (128) configured to cut tissue clamped between the distal portions of stapler halves (12, 14).

Each actuator (114, 116) of firing assembly (110) is configured and rotatable relative to slide block (112) between a deployed position and a retracted position such that only one actuator (114, 116) may be deployed at a time, for example as disclosed in U.S. Pat. No. 10,898,187, incorporated by reference above. In the deployed position, an actuator (114, 116) may be driven distally by an operator to actuate firing assembly (110) distally through stapler (10) and thereby simultaneously cut and staple tissue clamped between stapler halves (12, 14).

B. Illustrative Use of Linear Surgical Stapler

Figure 5:
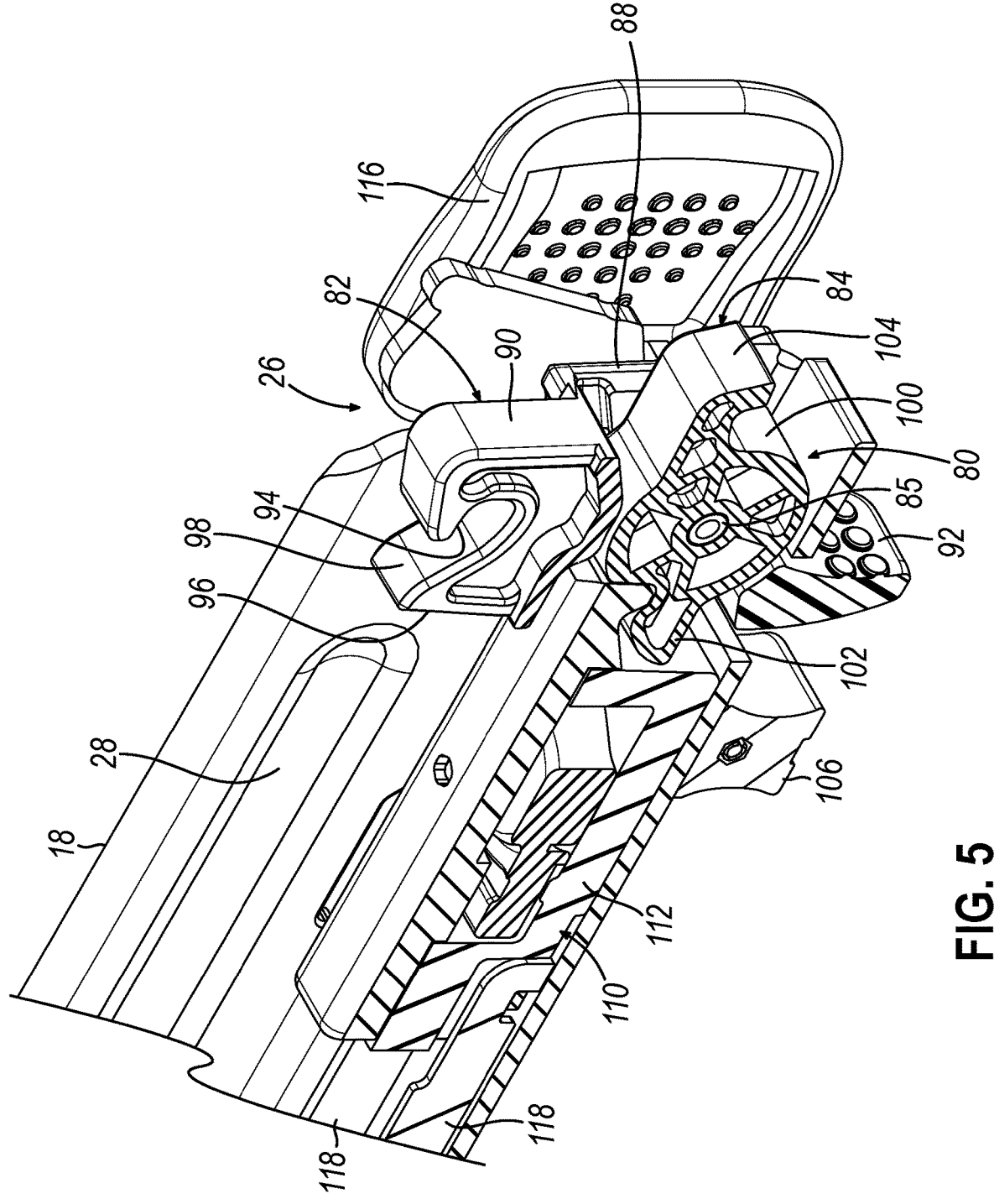
FIG. 5 depicts a cross-sectional perspective view of a proximal portion of the cartridge half of the linear surgical stapler of FIG. 1 with the clamp lever in an open position to reveal details of a firing assembly and a retaining assembly of the cartridge half.
Figure 6:
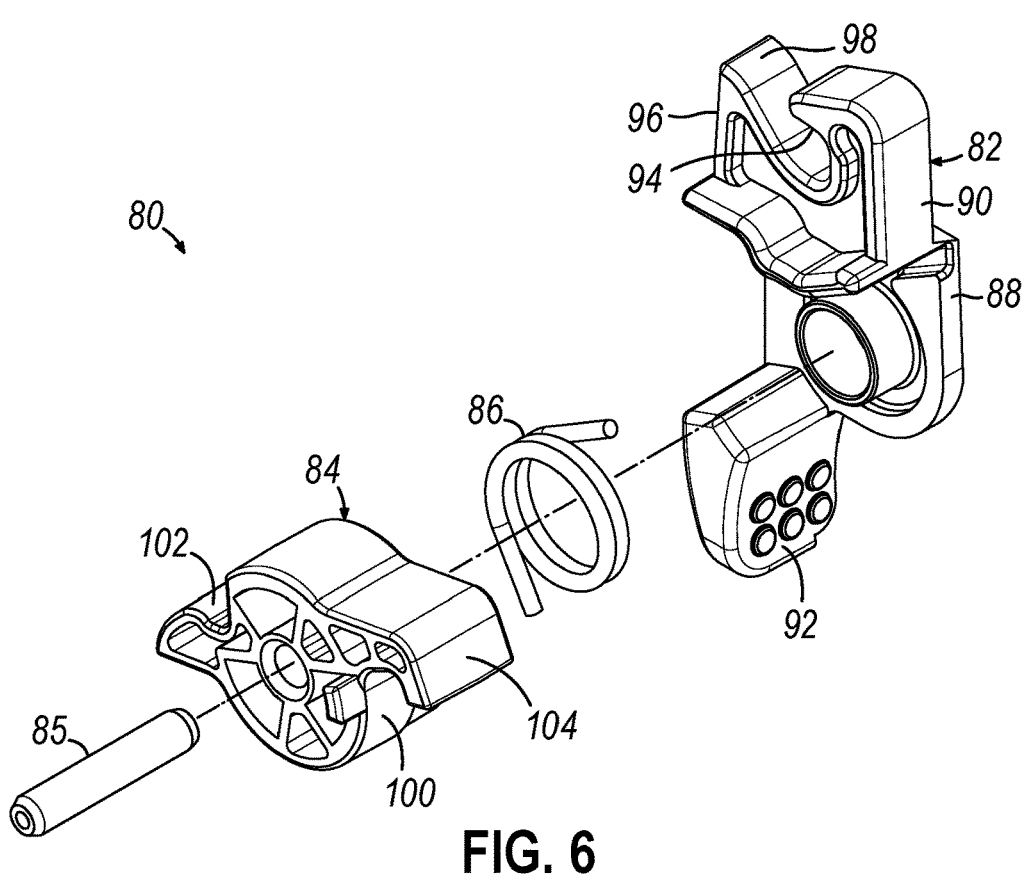
FIG. 6 depicts an exploded perspective view of the retaining assembly of FIG. 5.
Figure 7:
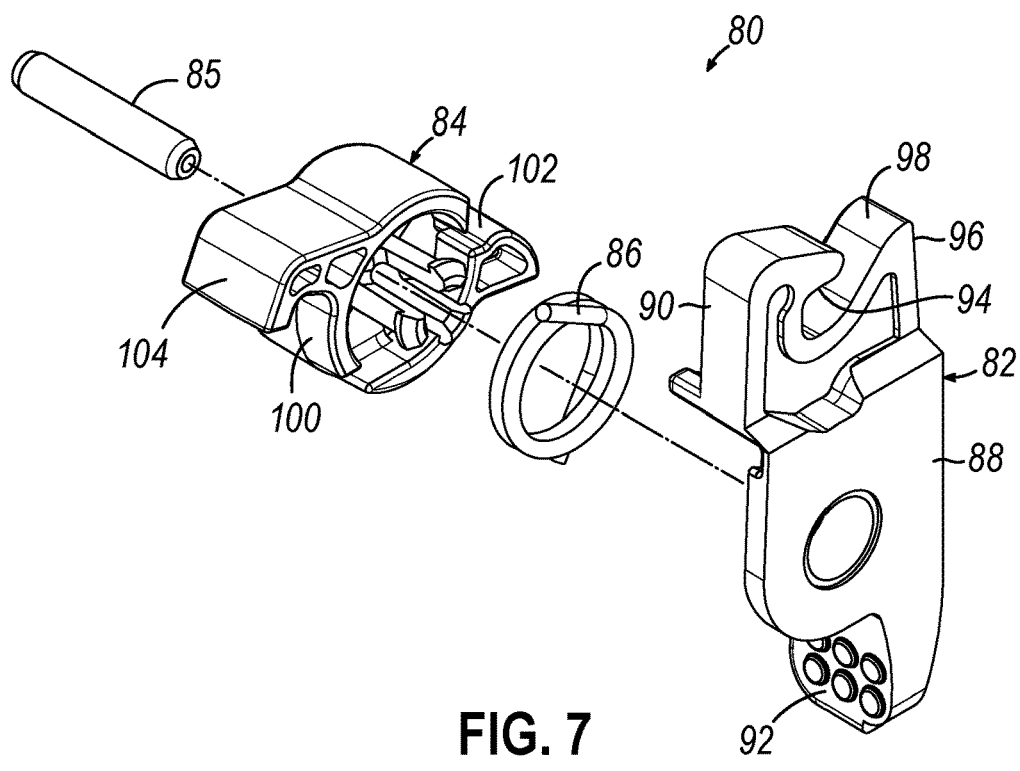
FIG. 7 depicts another exploded perspective view of the retaining assembly of FIG. 5.

FIGS. 9A-9E show illustrative coupling of stapler halves (12, 14) and subsequent firing of assembled stapler (10) during a surgical procedure. As shown in FIG. 9A, clamp lever (40) of cartridge half (12) is provided in the open position so that jaw slots (50) align with vertical slots (24)

of cartridge channel side flanges (22). Additionally, firing assembly (110) is maintained in its proximal home position by detent member (84) of retaining assembly (80), as shown in FIG. 5 described above. At this stage, a section of tissue (not shown) to be stapled and cut may be positioned over the top of staple cartridge (140) disposed in distal jaw portion (20) of cartridge half (12). Alternatively, the tissue may be positioned over staple cartridge (140) following coupling of the proximal ends of stapler halves (12, 14), described below.

As shown in FIGS. 9A-9B, the proximal ends of stapler halves (12, 14) are aligned with one another, and proximal anvil pin (70) is directed downwardly into proximal tapered notches (26) of cartridge channel (16) to engage latch finger (90) of anvil latch member (82). This engagement forces anvil latch member (82) to resiliently rotate clockwise, thus enabling latch finger (90) to capture anvil pin (70) and thereby releasably couple together the proximal ends of stapler halves (12, 14), as seen in FIG. 9B. With clamp lever (40) still in the open position as shown in FIG. 9B, stapler (10) is provided in a "hang-open" state such that stapler (10) may be held single-handedly by anvil half (14) while cartridge half (12) remains coupled to anvil half (14). As shown in FIG. 9C, and with clamp lever (40) remaining in the open position, anvil half (14) is rotated toward anvil half (14) about proximal anvil pin (70) so that distal latch pin (68) of anvil half (14) is received into vertical slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

As shown in FIG. 9D, clamp lever (40) is closed to draw anvil latch pin (68) against the closed proximal ends of jaw slots (50) and thereby fully clamp anvil half (14) against cartridge half (12), with tissue (not shown) clamped between the stapling surfaces defined by staple cartridge (140) and anvil plate (72). A slight transverse gap is defined between staple cartridge (140) and anvil plate (72) by a tissue gap post (162) of staple cartridge (140), thus accommodating the tissue therebetween with a predetermined degree of tissue compression. As shown in FIGS. 9A and 9B, tissue gap post (162) is disposed at a distal end of staple cartridge (140) and is configured to contact a distal end of anvil plate (72) when stapler (10) is in the fully clamped state shown in FIG. 19D. In response to clamp lever (40) reaching the fully closed position, clamp lever latch member (54) may rotate to capture a proximal end of a base wall of cartridge channel (16) and thereby assume a latched state in which clamp lever latch member (54) maintains clamp lever (40) in the closed position.

As shown in FIG. 19E, upon reaching the fully clamped state, stapler (10) may be fired by driving a deployed actuator (114, 116) of firing assembly (110) distally along proximal frame portion (18) of cartridge half (12). This action causes elongate beams (118, 122) of firing assembly (110) to translate distally through corresponding channels formed in staple cartridge (140) and thereby fire staples into the clamped tissue via cam ramps (120) and staple drivers (not shown), and simultaneously cut the clamped tissue with knife member (126). Following completion of the firing stroke, firing assembly (110) is returned to its proximal home position via the actuator (114, 116). Clamp lever latch member (54) may then be depressed to release the proximal end of clamp lever (40) from cartridge channel (16), thus permitting clamp lever (40) to be re-opened. Then, release button (92) of retaining assembly (80) may be depressed to release anvil half (14) from cartridge half (12) so that stapler halves (12, 14) may be separated from one another, thereby releasing the newly stapled and severed tissue. It will be understood that in some versions, stapler (10) may include additional features to promote decoupling of stapler halves (12, 14), for example as disclosed in U.S. Pat. No. 11,033, 266, incorporated by reference above.

C. Linear Surgical Stapler Having Clamp Load Measuring Capabilities

As mentioned above, anvil latch pin (68) of anvil half (14) is received within curved slots (50) of jaws (48) such that clamp lever (40) may pivot from the open position toward the closed position to thereby clamp anvil half (14) toward cartridge half (12) to thereby grasp tissue. Further, grasped tissue located between the stapling surfaces of staple cartridge (140) and anvil plate (72) may be severed and stapled.

In some instances, tissue grasped and clamped between staple cartridge (140) and anvil plate (72) may be too thick such that an undesirably large gap distance (d) is defined between staple forming pockets (74) of anvil plate (72) and deck (156) of cartridge (140). If gap distance (d) is too large, staples fired from staple cartridge toward anvil plate (72) may not suitably form, either creating malformed staples or "open" staples, either of which fail to suitably engage staple forming pockets (74) of anvil plate (72). In instances where grasped tissue creates a large gap distance (d), distal jaw portion (64) of elongated anvil channel (60), as well as components utilized to clamp distal jaw portion (64) (e.g., clamp lever (40)) may become subject to large closure forces in order to clamp thicker tissue as compared to instances where an appropriate tissue thickness is clamped. Therefore, it may be desirable to monitor parameters that are indicative of large closure forces imparted on distal jaw portion (64) while clamping tissue in accordance with the teachings herein in order to determine and/or indicate risk of malformed or open staples.

As mentioned above, clamp lever (40) is utilized to drive distal jaw portion (64) of elongated anvil channel (60) to clamp tissue via engagement between curved slots (50) of jaws (48) and anvil latch pin (68) of anvil channel (60). As jaws (48) of clamp lever (40) drive anvil latch pin (68) from the position shown in FIG. 9C into the latched condition shown in FIG. 9D, jaws (48) and other components of clamp lever (40) experience forces that correlate to the clamping load imparted on distal jaw portion (64) via clamping tissue.

Forces experienced by jaw (48) and components of clamp lever (40) may lead to strain deformation. The value of strain deformation of jaws (48) may be indicative of the closure forces acting on distal jaw portion (64) during illustrative use in accordance with the teachings herein. As mentioned above, if such closure forces are too high, this may be indicative of too large a gap distance (d) caused by too thick tissue.

Figure 10:
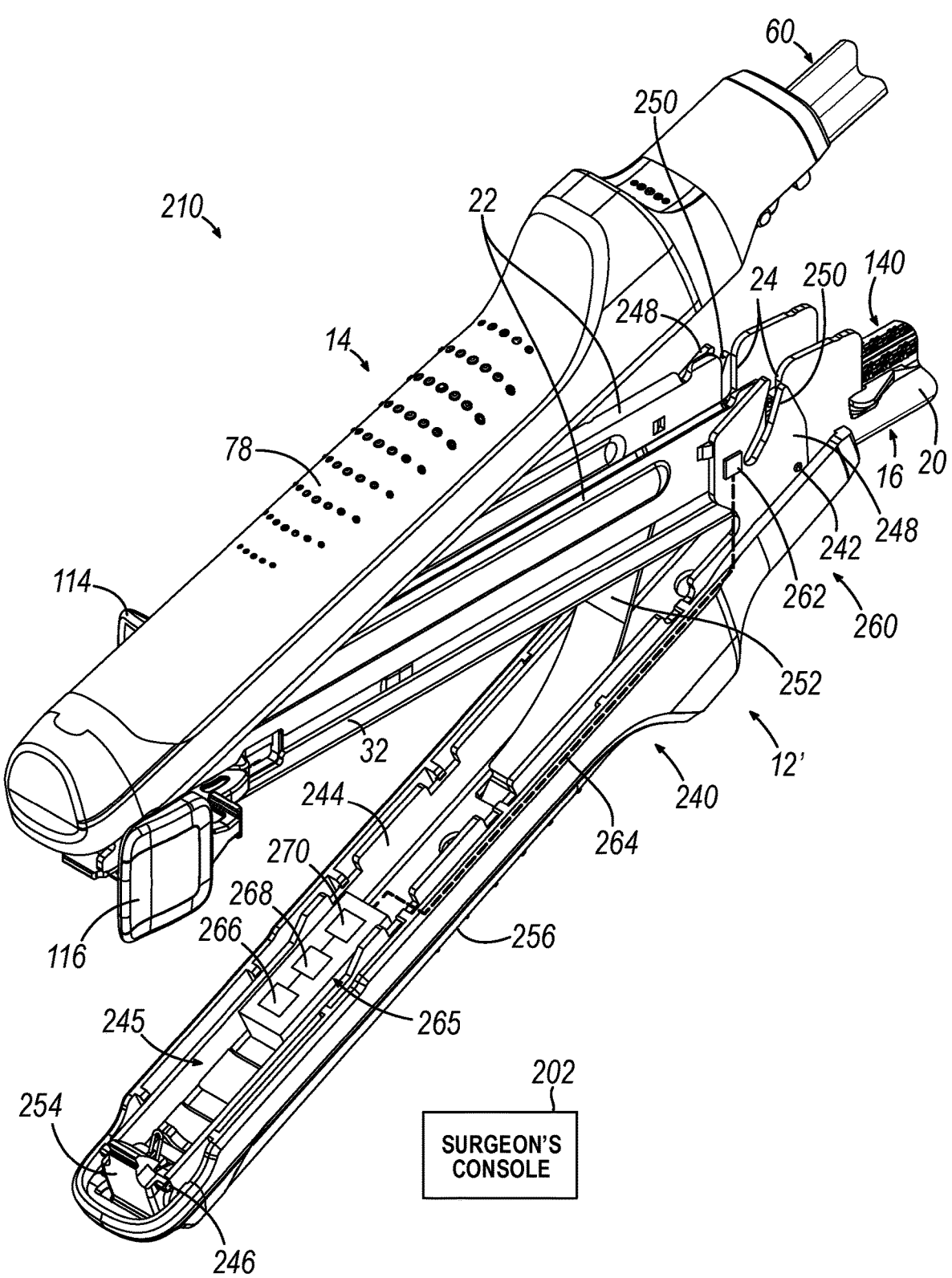
FIG. 10 depicts a rear perspective view of a proximal portion of an alternative liner surgical stapler, showing proximal ends of a cartridge half and an anvil half of the stapler coupling together while a clamp lever is in an open position to provide the stapler in a "hang-open" state.

FIG. 10 shows an alternative illustrative linear surgical stapler (210) that is substantially similar to linear surgical stapler (10) described above, with differences elaborated below. Therefore, linear surgical stapler (210) includes cartridge half (12'), anvil half (14), elongated cartridge channel (16), anvil channel (60), firing assembly (110), and replaceable staple cartridge (140). Cartridge half (12') is substantially similar to cartridge half (12) described above, except cartridge half (12') includes an alternative clamp lever (240) in replacement of clamp lever (40) described above.

Clamp lever (240) is substantially similar to clamp lever (40) described above, with differences elaborated herein. Therefore, clamp lever (240) includes a clamp lever pivot pin (242), an elongated lever arm (244), a free proximal end (246), a pair of opposed jaws (248) each defining a curved slot (250), a leaf spring (252), latch member (254) and a shroud (256); which are substantially similar to clamp lever pivot pin (42), elongated lever arm (44), free proximal end (46), opposed jaws (48), curved slot (50), leaf spring (52), latch member (54), and shroud (56) described above, respectively.

Additionally, clamp lever (240) includes a clamp lever strain measuring assembly (260). As will be described in greater detail below, clamp lever strain measuring assembly (260) is configured to measure the strain on at least one jaw (248) of clamp lever (240) adjacent to anvil latch pin (68) as clamp arm (240) is pivoted from the open position shown in FIG. 12A into the closed position shown in FIG. 12B in order to clamp tissue during illustrative use. The measured strain on jaw (248) of clamp lever (240) may be indicative of the closure forces acting on distal jaw portion (64) while clamping tissue. Additionally, clamp lever strain measuring assembly (260) and/or surgeon's console (202) is/are configured to compare the measured strain to one or more predetermined limit(s) and determine/communicate the risk of fired staples being malformed/open based on the comparison.

Surgeon's console (202) may include a visual display that may be referenced by a surgeon during a surgical procedure. Console (202) may display suitable information to a surgeon during a procedure. Console (202) may include the necessary computing power, storage, communication means, display features, etc., as would be apparent to one skilled in the art in view of the teachings herein.

Figure 11:
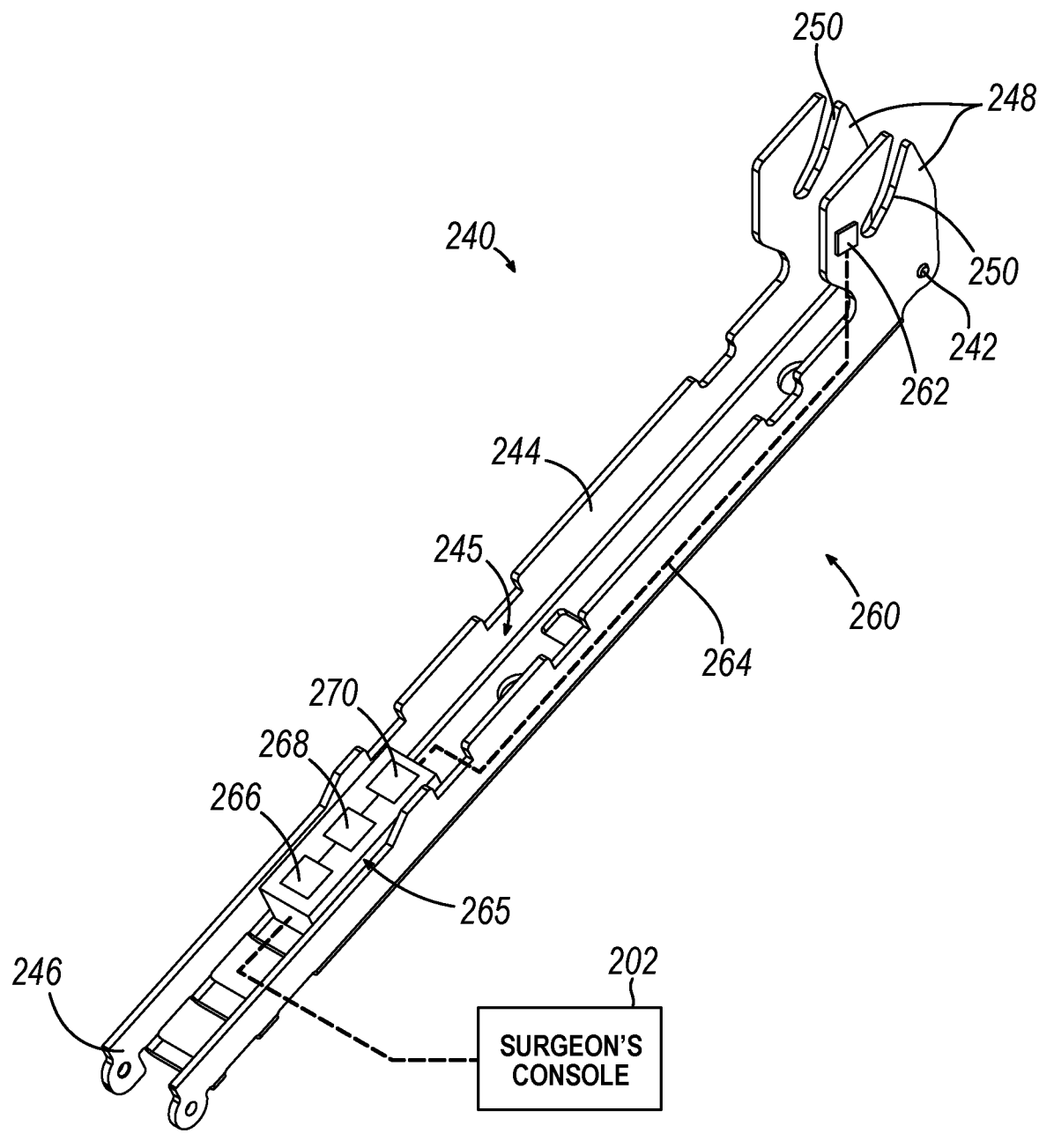
FIG. 11 depicts a perspective view of clamp lever strain measuring assembly associated with a portion of the clamp lever of FIG. 10.

Turning to FIG. 11, clamp lever strain measuring assembly (260) includes a strain gauge (262) and an electronic unit (265) operatively connected to each other via one or more electrical communication lines(s) (264). Strain gauge (262) is suitably attached to a portion of jaw (248) defining curved slot (250) such that strain gauge (262) is located along a portion of jaw (248) that is adjacent to anvil latch pin (68) during illustrative clamping of tissue in accordance with the teaching herein. Strain gauge (262) is configured to measure the strain value at respective portions of jaw (248) in response to jaws (248) driving anvil latch pin (68) into the clamped configuration (see FIG. 12B). It should be understood that larger clamping forces required to suitably grasp tissue will result in larger measured strain values; while smaller clamping forces required to suitably grasp tissue will result in smaller strain values. Strain gauge (262) may include any suitable components and geometry as would be apparent to one skilled in the art in view of the teachings herein. Further, strain gauge (262) may be attached to jaw (248) of clamp lever (240) using any suitable means as would be apparent to one skilled in the art in view of the teachings herein. While one strain gauge (262) on one jaw (248) is used in the current example, any suitable number of strain gauges (262) may be used on one or both jaws (248) as would be apparent to one skilled in the art in view of the teachings herein.

Deviations in strain measurements of jaw (248) in response to driving elongated anvil (60) to grasp and clamp tissue may be the largest (i.e., more pronounced) at portions of jaw (248) adjacent to curved slot (250) that engages anvil latch pin (68)). Therefore, strain gauge (262) being located at or around portions of portions of jaw (248) adjacent to curved slot (250) may provide the benefit of measuring strain deviations associated with, or strongly indicative to, clamp lever (40) driving anvil channel (60) into a clamped configuration during illustrative use in accordance with the description herein.

As mentioned above, strain gauge (262) is in operative commutation with electronic module (265) via electrical communication line(s) (264). Therefore, communication lines (264) extend along elongated lever arm (244) between strain gauge (262) and electronic module (265). Strain gauge (262) is configured to communicate the strain signal indicative of the measured strain value to electronic module (265).

Electronic unit (265) is housed within an internal recess (245) defined by elongated lever arm (244). Electronic unit (265) is positioned within internal recess (245) such that as clamp lever (240) is pivoted relative to proximal frame portion (18) from the open position (see FIG. 12A) into the closed position (see FIG. 12B), electronic unit (265) is not damaged via contact with other components of linear surgical stapler (210). Electronic unit (265) may be coupled to elongated lever arm (244) via any suitable means as would be apparent to one skilled in the art in view of the teaching herein.

Electronic unit (265) includes a control unit (266), a wireless transmitter (268), and a battery (270), each in suitable communication with each other. Battery (270) is configured to electrically power the necessary components of anvil strain measuring assembly (260). Battery (270) may include any suitable components as would be apparent to one skilled in the art in view of the teachings herein. In some instances, battery (270) may be connected to a switch (or other suitable mechanism) configured to selectively activate battery (270) such that a user may selectively activate anvil strain measuring assembly (260). Such a switch may be present on the outer surface of electronic unit (265) or any other suitable location. Therefore, a user may activate clamp lever strain measuring assembly (260) prior to illustrative use. Of course, battery (276) may be configured to activate clamp lever strain measuring assembly (260) in response to any other suitable activation method as would be apparent to one skilled in the art in view of the teachings herein.

Control unit (266) is configured to suitably process the measured strain from strain gauge (262) in accordance with the description herein, while wireless transmitter (268) is configured to suitably transmit information (e.g., the measured strain received by control unit (226)) between control unit (266) and surgeon's console (202). Control unit (266) and wireless transmitter (268) include any suitable electrical components necessary to perform the recited function herein. Control assembly (224) may include printed circuit board (PCB), suitable memory, and/or suitable processing means to function in accordance with the description herein. Wireless transmitter (268) may include a Bluetooth transmitter, or any other suitable wireless technology as would be apparent to one skilled in the art in view of the teachings herein.

A first predetermined limit stored on control unit (266) may be indicative of clamp lever (40) applying the necessary clamping force to clamp tissue having a maximum acceptable tissue thickness associated with a generally acceptable maximum gap distance. If the measured strain value from strain gauge (262) is above the first predetermined limit, this may be indicative that the clamped tissue between deck (156) (see FIG. 12B) and anvil plate (72) is too thick and creates a gap distance (d) greater than the generally acceptable maximum gap distance. In other words, if the measured strain value is above the first predetermined limit, this may be indicative that fired staples have an unacceptably high risk of being malformed or open.

Control unit (266) may store predetermined limit(s) for surgical stapler (210) and communicate the predetermined limit(s) to surgeon's console (202) via wireless transmitter (268) such that surgeon's console (202) may utilize the predetermined limit(s) in accordance with the description herein. Additionally, or alternatively, control unit (266) may utilize the self-stored predetermined limit(s) and process the measured strain from stain gauge (262) in accordance with the description herein. In such instances, control unit (266) may transfer its calculations to surgeon's console (202) to be displayed to a user. Yet in other instances, surgeon's console (202) may already have predetermined limit(s) preloaded such that communication of the predetermined limit from control unit (266) to console (202) is not necessarily required.

Figure 12A:
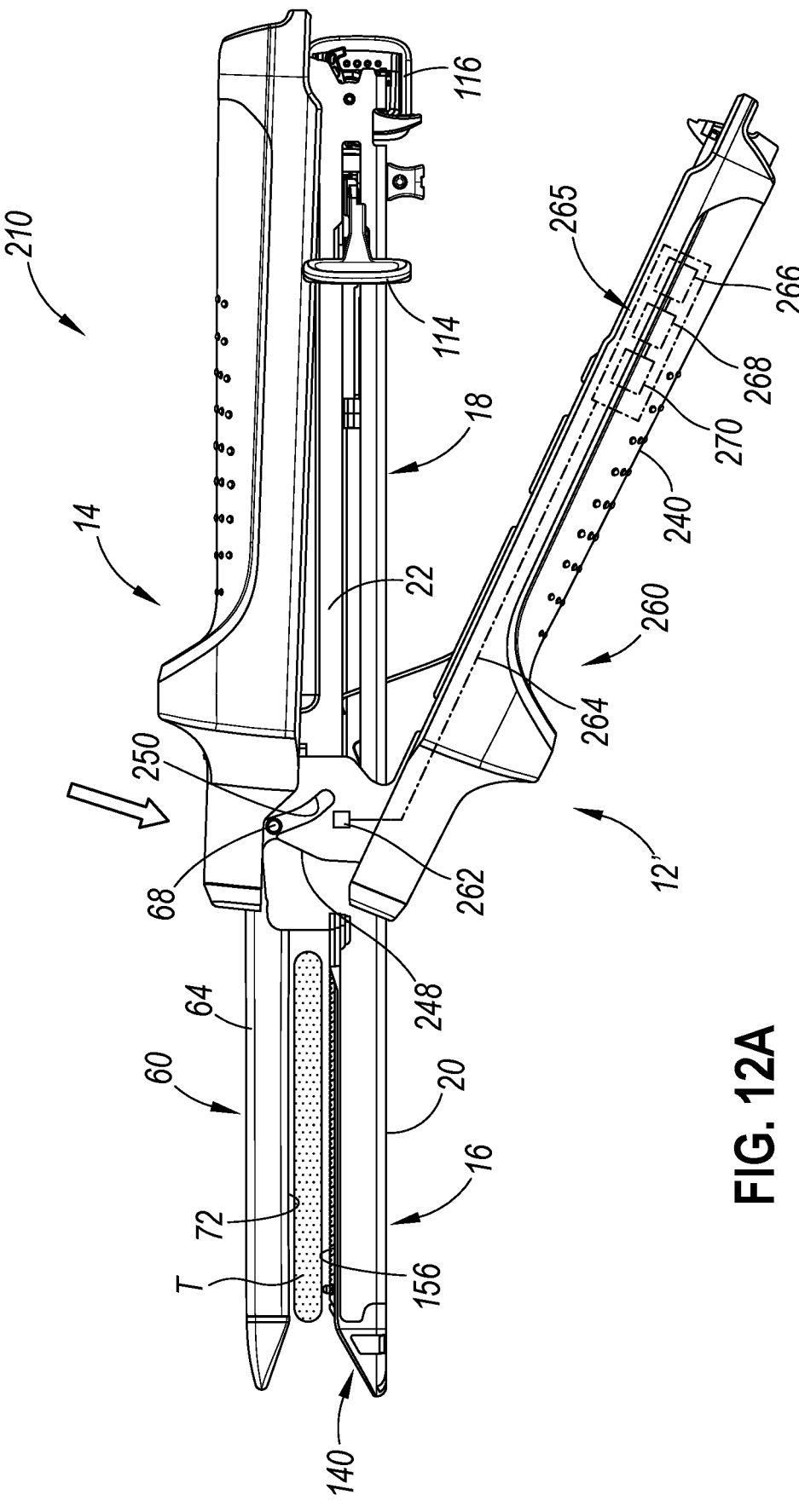
FIG. 12A depicts a side elevational view of the liner surgical stapler of FIG. 10, showing distal portions of the stapler halves having been approximated so that a distal pin of the anvil half is received by clamp lever jaws of the cartridge half.
Figure 12B:
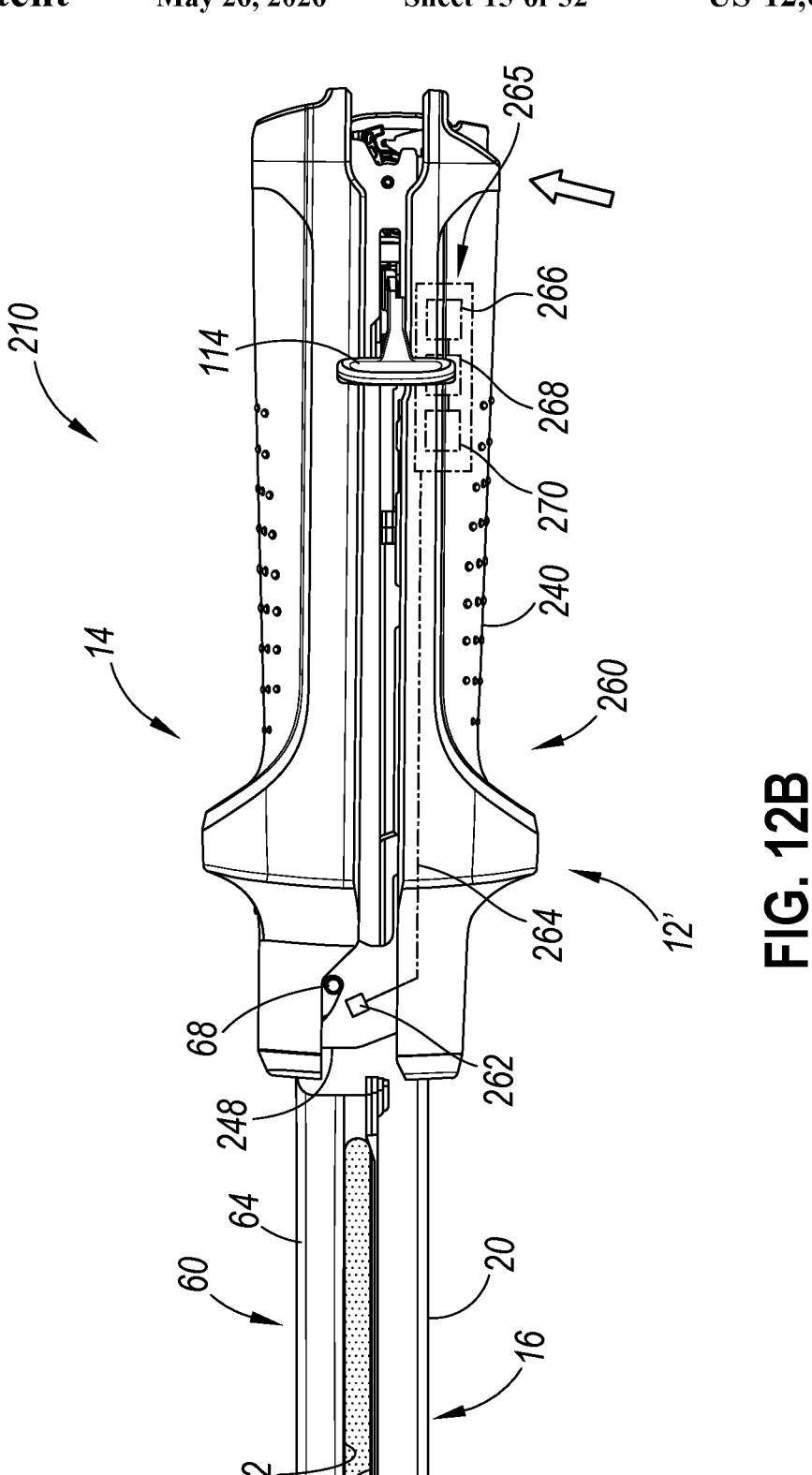
FIG. 12B depicts a side elevational view of the liner surgical stapler of FIG. 10, showing closure of the clamp lever to fully clamp the stapler halves together.
Figure 13:
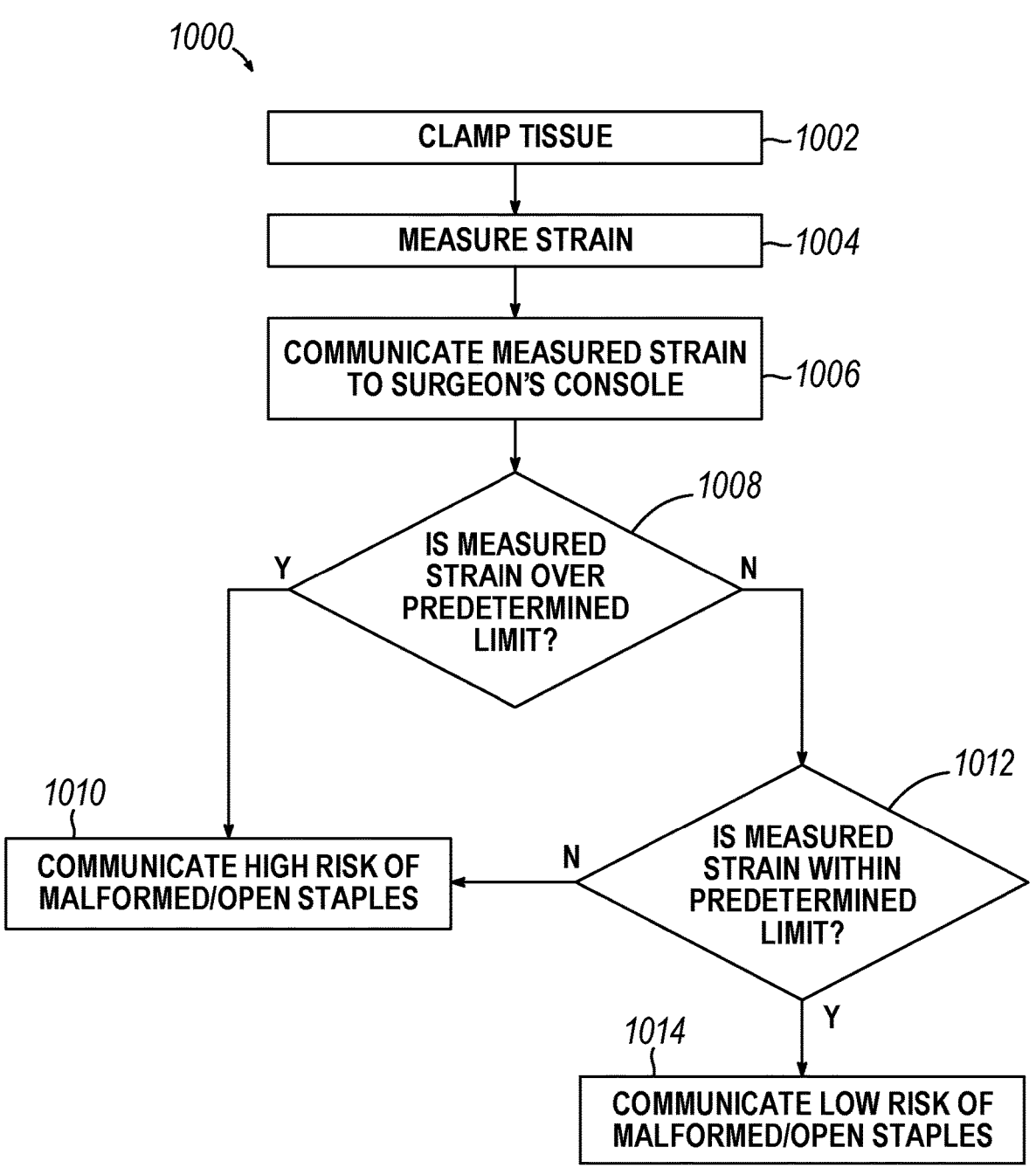
FIG. 13 depicts a flowchart of an exemplary method of use of a linear surgical stapler having a clamp lever strain measuring assembly.
Figure 14:
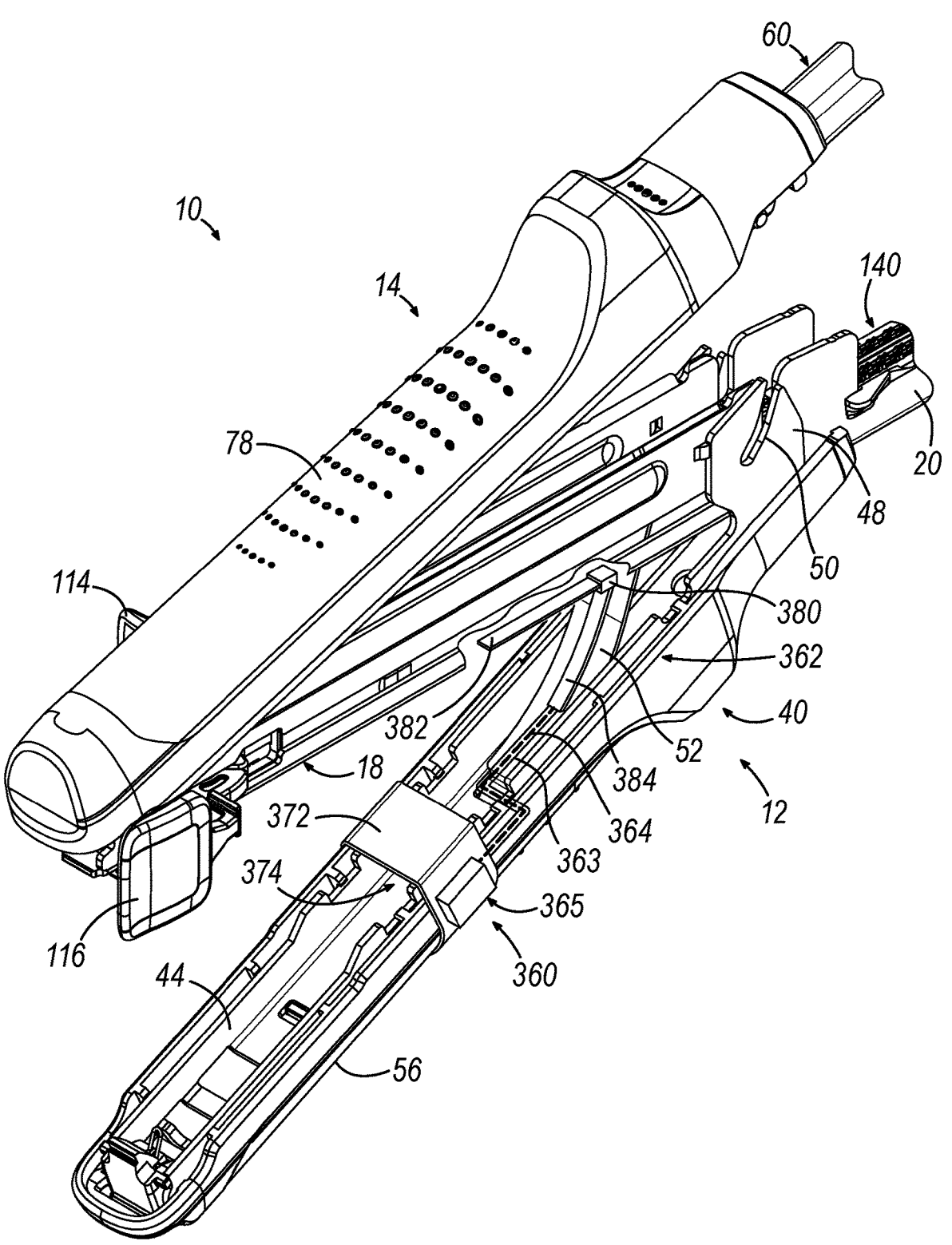
FIG. 14 depicts a rear perspective view of a proximal portion of an alternative liner surgical stapler, showing proximal ends of a cartridge half and an anvil half of the stapler coupling together while a clamp lever is in an open position to provide the stapler in a "hang-open" state.

FIGS. 12A-12B show an illustrative use of surgical stapler (210) to clamp tissue, while FIG. 14 shows an illustrative method (1000) of clamp lever strain measuring assembly (260) and console (202) determining if a suitable gap distance (d) is present such that the risk of malformed/open fired staples is low; or if an unsuitable gap distance (d) is present such that the risk of malformed/open fired staples is high. First, a user may clamp tissue (1002) between deck (156) of staple cartridge (140) and anvil plate (72) of elongate anvil channel (60) by utilizing clamp lever (240) in accordance with the teachings herein. In such an instances, anvil latching pin (68) is driven into the clamped configuration via suitable engagement with curved slot (250) defined by opposed jaws (248) of clamp lever (240). As mentioned above, generally, the thicker clamped tissue results in both larger clamping forces (and resulting larger strains on anvil channel (60)) and larger gap distance (d) between anvil plate (72) and deck (156).

While tissue is suitably clamped, strain gauge (222) of anvil strain measuring assembly (220) measures (1004) the resulting strain on portions of jaw (248) adjacent to curved slot (250) housing anvil latching pin (68). The measured (1004) strain is communicated to electronic module (265) such that control unit (266) receives the measurement. Control unit (266) may then send the measurement to wireless transmitter (268), which in turn wirelessly communicates (1006) the measurement to surgeon's console (202). Next, console (202) may process the received measurement by comparing (1008, 1012) the measured strain from strain gauge (262) to a predetermined limit stored on console (202). In this example, console (202) determines if the measured stain is over the predetermined limit (1008) and/or determines if the measured strain is within (e.g., below) the predetermined limit (1012). If the measured strain is above the predetermined limit, console (202) communicates (1010) to the user that a high risk of malformed and/or open staples exists if the user were to actuate firing assembly (110) with the current clamping status. Similarly, if the measured strain is outside the predetermined limit, console (202) communicates (1010) to the user that a high risk of malformed and/or open staples exists if firing assembly (110) were to be distally actuated (e.g., fired) with the current clamping status. However, if the measured strain is under the predetermined limit and/or within the predetermined range, console (202) communicates (1014) to the user that a low risk of malformed and/or open staples exits firing assembly (110) were to be distally actuated (e.g., fired) with the current clamping status.

In this illustrative use, it should be understood that control unit (266) may have sent item specific predetermined limit(s) determined and stored on control unit (266) during assembly of a specific item to surgeon's console (202). In some instances, surgeon's console (202) and/or control unit (266) may already have generic predetermined limits stored associated with a make and model of a surgical stapler.

While console (202) made the comparison (1008, 1012) in the current example, it should be understood that in some instances, control unit (266) may make the comparisons and communicate the results to console (202) to display to a user.

In some instances, it may be desirable to modify an exiting linear surgical stapler (10) to be operable in conjunction with surgeon's console (202) in order to determine a low risk or a high risk of malformed and/or open staples forming if a user actuated assembly (110) under such a clamping load. For example, it may be desirable to apply a measuring assembly to linear surgical stapler (10) in preparation of a surgical procedure that is configured to communicate with a surgeon's console (202) during illustrative use to provide feedback based on the measure clamping loads detected by the measuring assembly. In some instances, such application of measuring assembly could occur immediately prior to a surgical procedure at or near the location of the intended surgical procedure.

Figure 15A:
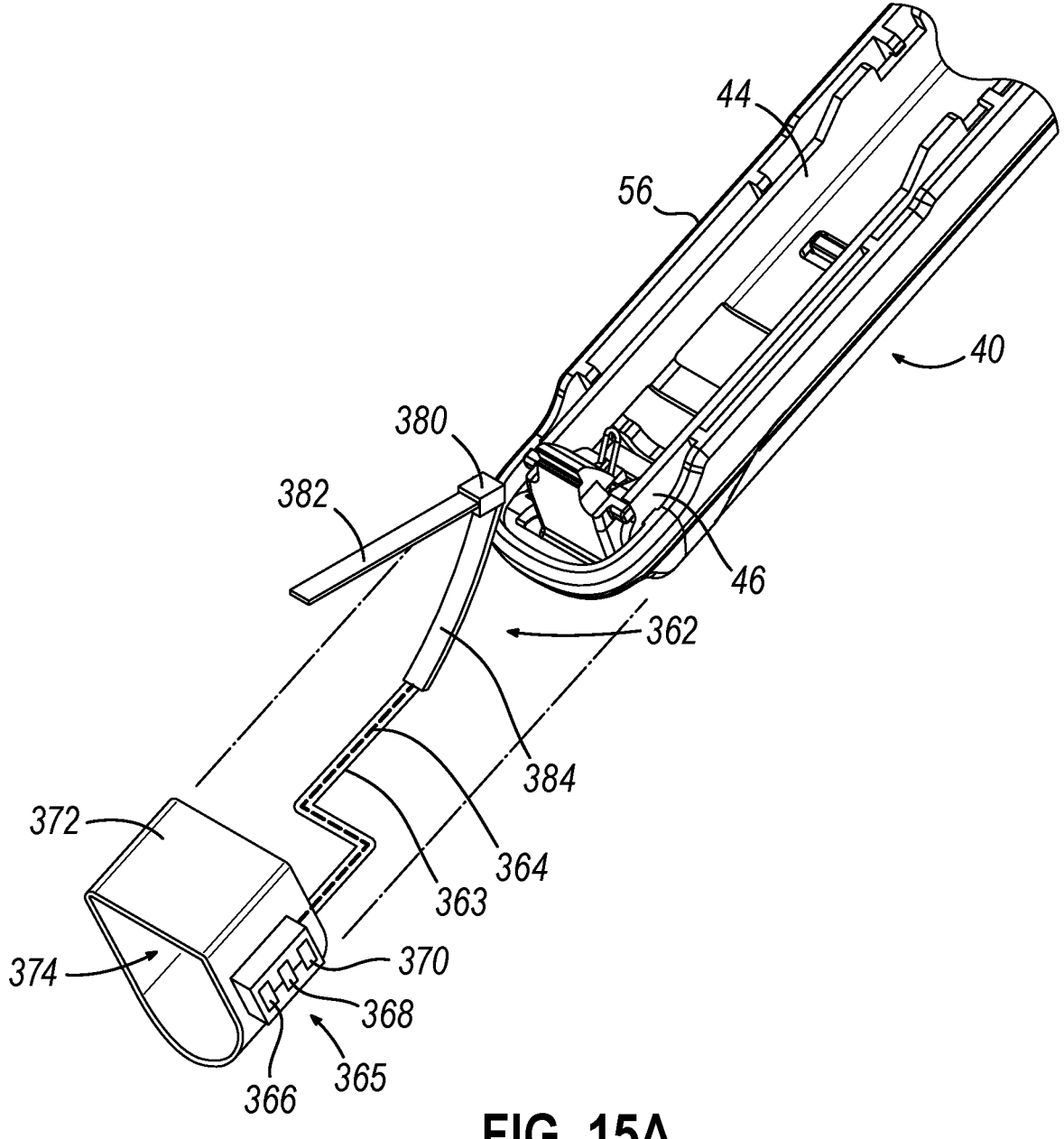
FIG. 15A depicts a perspective view of a clamp lever force measuring assembly of the linear surgical stapler of FIG. 14 detached from the clamp lever of FIG. 14.
Figure 15B:
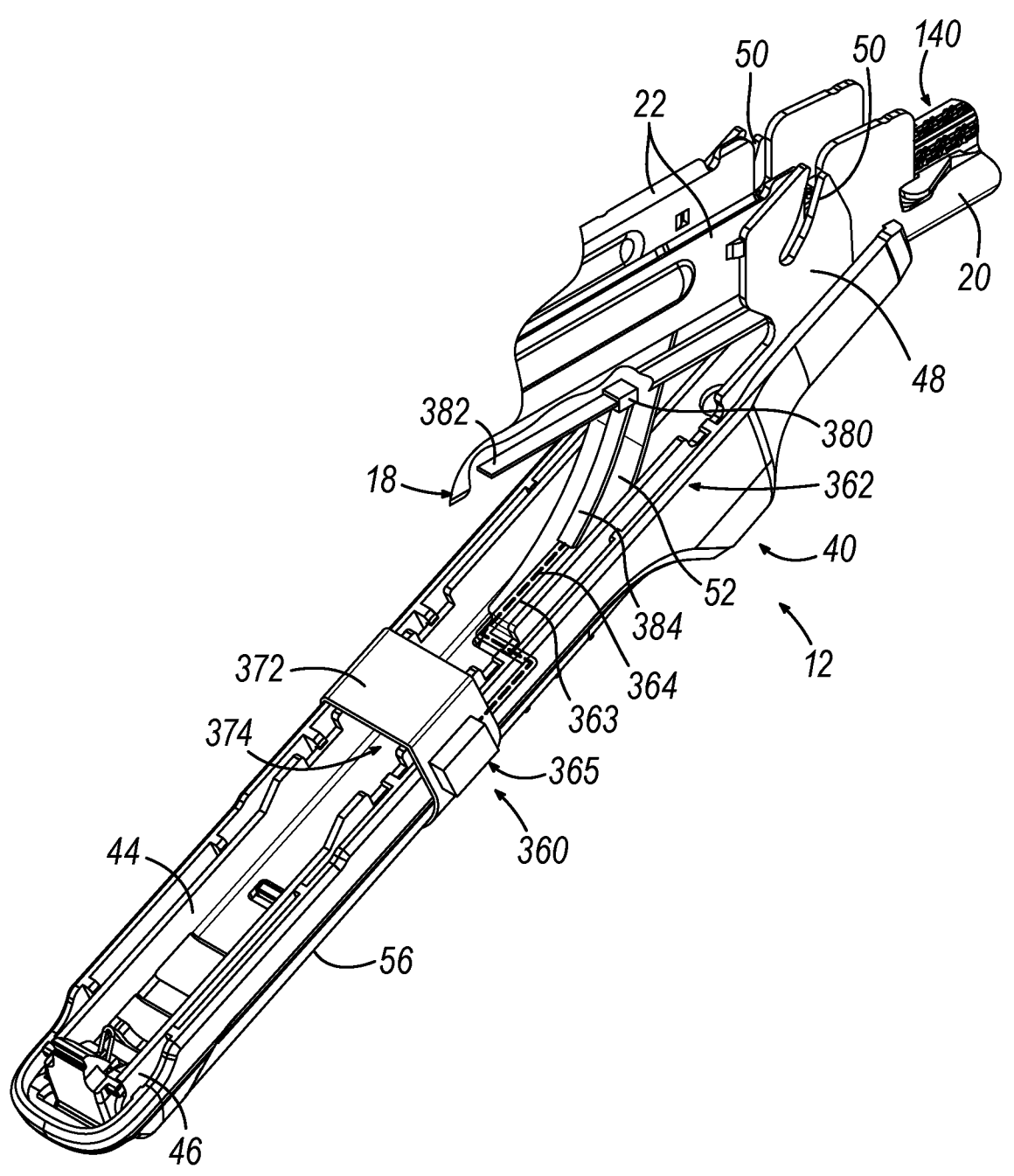
FIG. 15B depicts a perspective view of the clamp lever force measuring assembly of FIG. 15A attached to the clamp lever of FIG. 14.

FIGS. 14-15B show an illustrative clamp force measuring assembly (360) configured to be coupled to linear surgical stapler (10) in order to modify stapler (10) for illustrative use with surgeon's console (202). Once assembled onto linear surgical stapler (10), force measuring assembly (360) is configured to measure suitable parameters indicative of the closure force of distal jaw portion (64) and/or the gap distance (d) between deck (156) and anvil plate (72). Further, clamp force measuring assembly (360) is configured to communicate the measurements to surgeon's console (202) in order to display information related to such measurements to a user (e.g., level of risk of malformed/open staples forming).

Clamp force measuring assembly (360) includes a sensor unit (362) operatively attached to an electronic unit (365) housed within a flexible sleeve (372). Sensor unit (362) is attached to flexible sleeve (272) via a coupling body (363). Sensor unit (362) is in operative communication with electronic unit (365) via an electrical communication line (364) extending between sensor unit (362) and electronic unit (365) via coupling body (363). Coupling body (363) may be rigid, semi-rigid, flexible, resiliently flexible, etc. Coupling body (363) ensures sensor unit (362) remains in operative electrical communication with electronic unit (365). When measuring assembly (360) is suitably coupled with clamp lever (40), coupling body (363) extends within an interior of elongate lever arm (44).

Flexible sleeve (372) defines a through hole (374). Through hole (374) of flexible sleeve (372) is dimensioned to fit over a free proximal end (46) of clamp lever (40). Therefore, as shown between FIGS. 15A-15B, in order to couple measuring assembly (360) with clamp lever (40), a user may insert flexible sleeve (372) over proximal end (46) of clamp lever (40) and slide flexible sleeve (372) distally until sensor unit (362) engages suitable components of linear stapler (10) in accordance with the description herein. The interior surface of flexible sleeve (372) defining through hole (374) is configured to engage portions of clamp lever (40) with sufficient frictional braking force in order to promote coupling of sleeve (372) with clamp lever (40) once inserted to a desired longitudinal location along the length of clamp lever (40), as shown in FIG. 15B. In the current example, flexible sleeve (372) is formed of an elastomeric material that promotes the frictional braking force with engaged portions of clamp lever (40). Additionally, flexible sleeve (372) defines an interior chamber that houses electronic unit (365).

Electronic unit (365) is substantially similar to electronic unit (265) described above. Therefore, electronic unit (365)

includes a control unit (366), a wireless transmitter (368), and a battery (370); which are substantially similar to control unit (266), wireless transmitter (268), and battery (270) described above, respectively. As such, control unit (366) may store one or more predetermined limit(s) indicative of a maximum acceptable gap distances (d); while wireless transmitter (368) establishes communication with console (202).

Sensor unit (362) includes a first leg (382) and a second leg (384) each coupled to a sensor (380). First leg (382) is configured to selectively couple to the underside of proximal frame portion (18) when measuring assembly (360) is operatively attached to stapler (10). Second leg (384) is configured to selectively couple to leaf spring (52) of clamp lever (40) when measuring assembly (360) is operatively attached to stapler (10). Once measuring assembly (360) is suitably coupled to stapler (10), legs (382, 384) are configured to pivot relative to each other in response to clamp lever (40) pivoting about clap lever pivot pin (42) in order to clamp tissue in accordance with the description herein. Each leg (382, 384) is in operative communication with sensor (380). Sensor (380) is configured to measure a suitable parameter indicative of gap distance (d) and/or closure force imparted on distal jaw portion (64) while clamping tissue. Sensor (380) communicates measurements to electronic unit (365) via electrical communication line (364).

As one example, sensor (380) may measure the angle between legs (382, 384), as the angle between legs (382, 384) is indicative of the angle between clamp lever (40) and proximal frame portion (18). Since the angle between clamp lever (40) and proximal frame portion (18) is also indicative of gap distance (d), such a measurement can be utilized in order to determine if gap distance (d) is within an acceptable range for suitable formation of staples (i.e., a low risk of malformed or open staples if firing assembly (110) were to be actuated distally with the determined gap distance (d)). A predetermined limit associated with the angle between clamp lever (40) and proximal frame portion (18) indicative of a maximum acceptable gap distance (d) may be used in such examples.

As another example, sensor (280) may be configured to measure the relative forces imparted on legs (382, 384) while clamp lever (40) is utilized to clamp tissue. Force acting on clamp lever (40) while clamping tissue correlates with the closure forces acting on distal jaw portion (64). Such a measurement can be utilized in order to determine if gap distance (d) is within an acceptable range for suitable formation of staples (i.e., a low risk of malformed or open staples if firing assembly (110) were to be actuated distally with the determined gap distance (d)). Sensor (380) may have any suitable components as would be apparent to one skilled in the art in view of the teachings herein. Sensor (380) may include a strain gauge sensor, an angle sensor, a tilt sensor, etc. A predetermined limit associated with the force acting on clamp lever (40) indicative of a maximum acceptable gap distance (d) may be used in such examples.

Figure 16A:
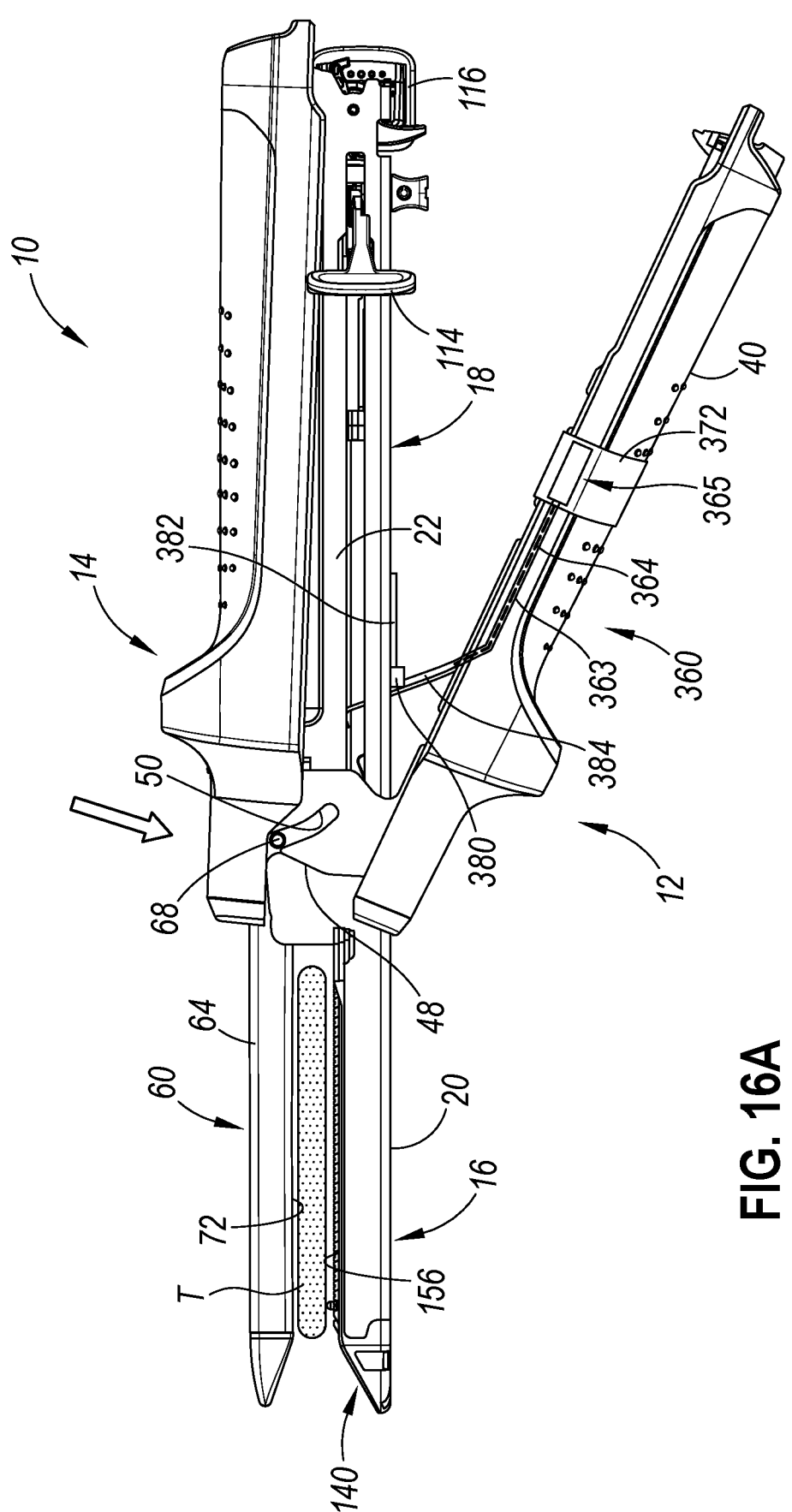
FIG. 16A depicts a side elevational view of the linear surgical stapler of FIG. 14, showing distal portions of the stapler halves having been approximated so that a distal pin of the anvil half is received by clamp lever jaws of the cartridge half.
Figure 16B:
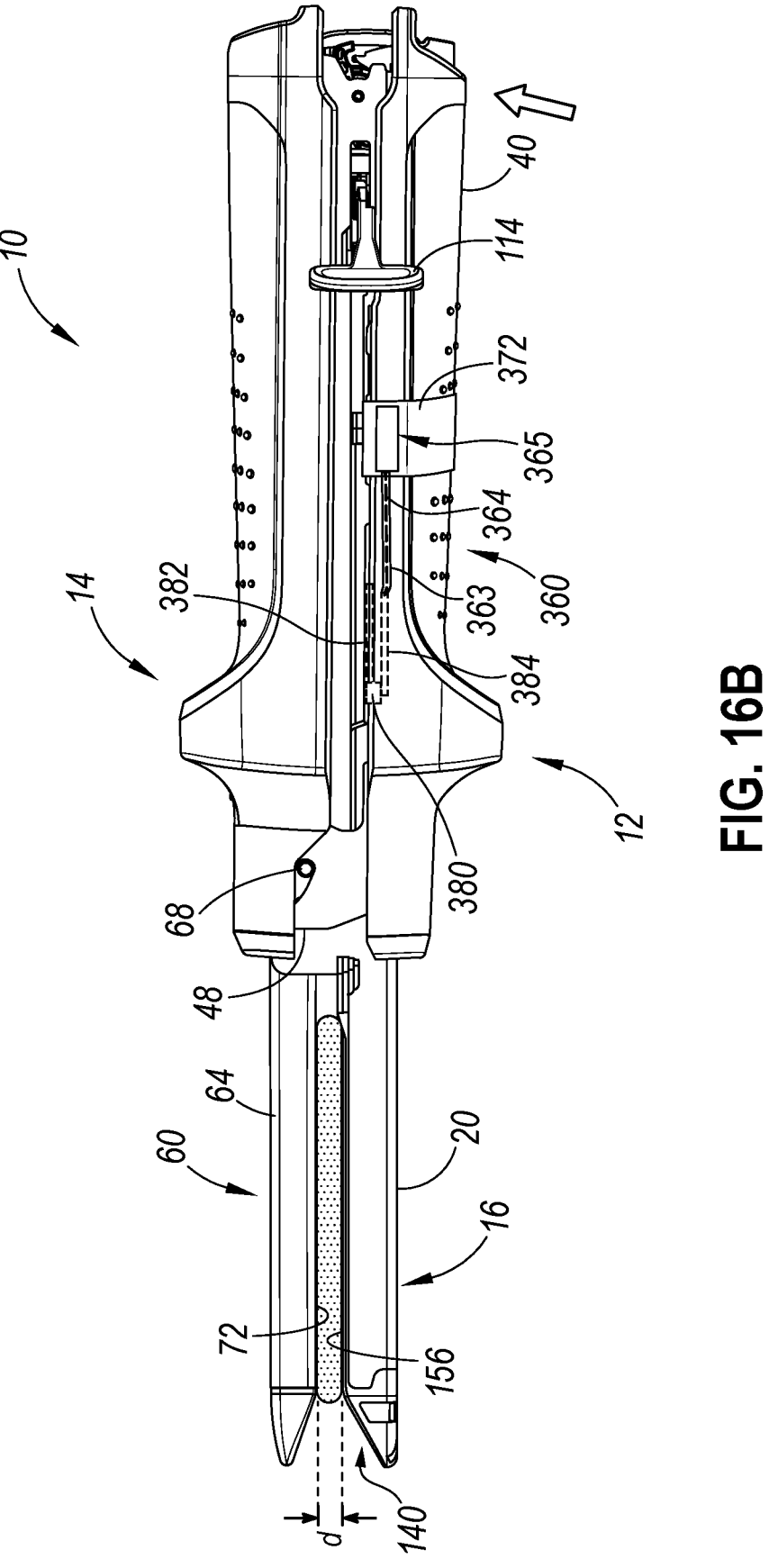
FIG. 16B depicts a side elevational view of the linear surgical stapler of FIG. 14, showing closure of the clamp lever to fully clamp the stapler halves together.
Figure 17:
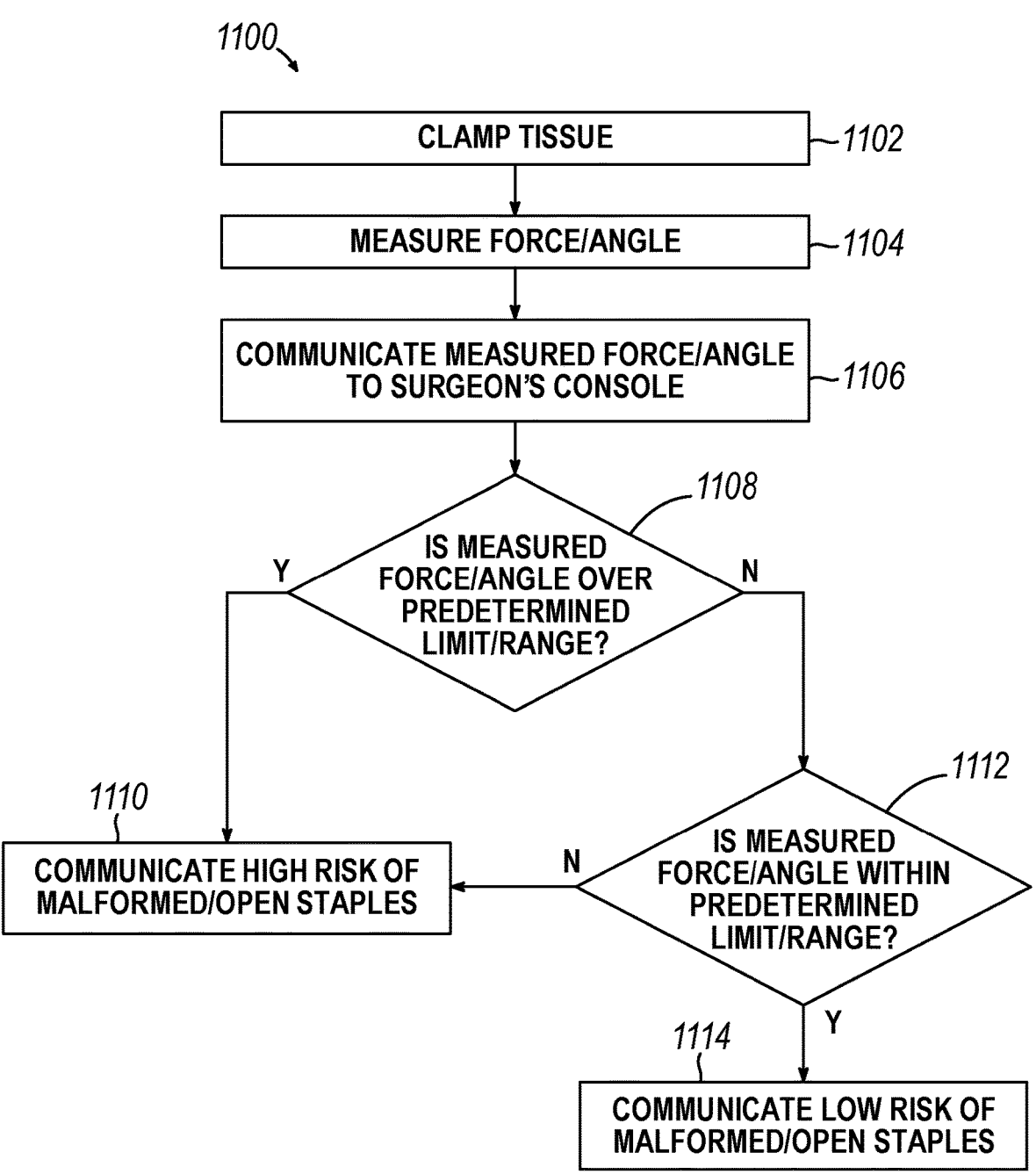
FIG. 17 depicts a flowchart of an exemplary method of use of a linear surgical stapler having a clamp lever force measuring assembly.
Figure 18A:
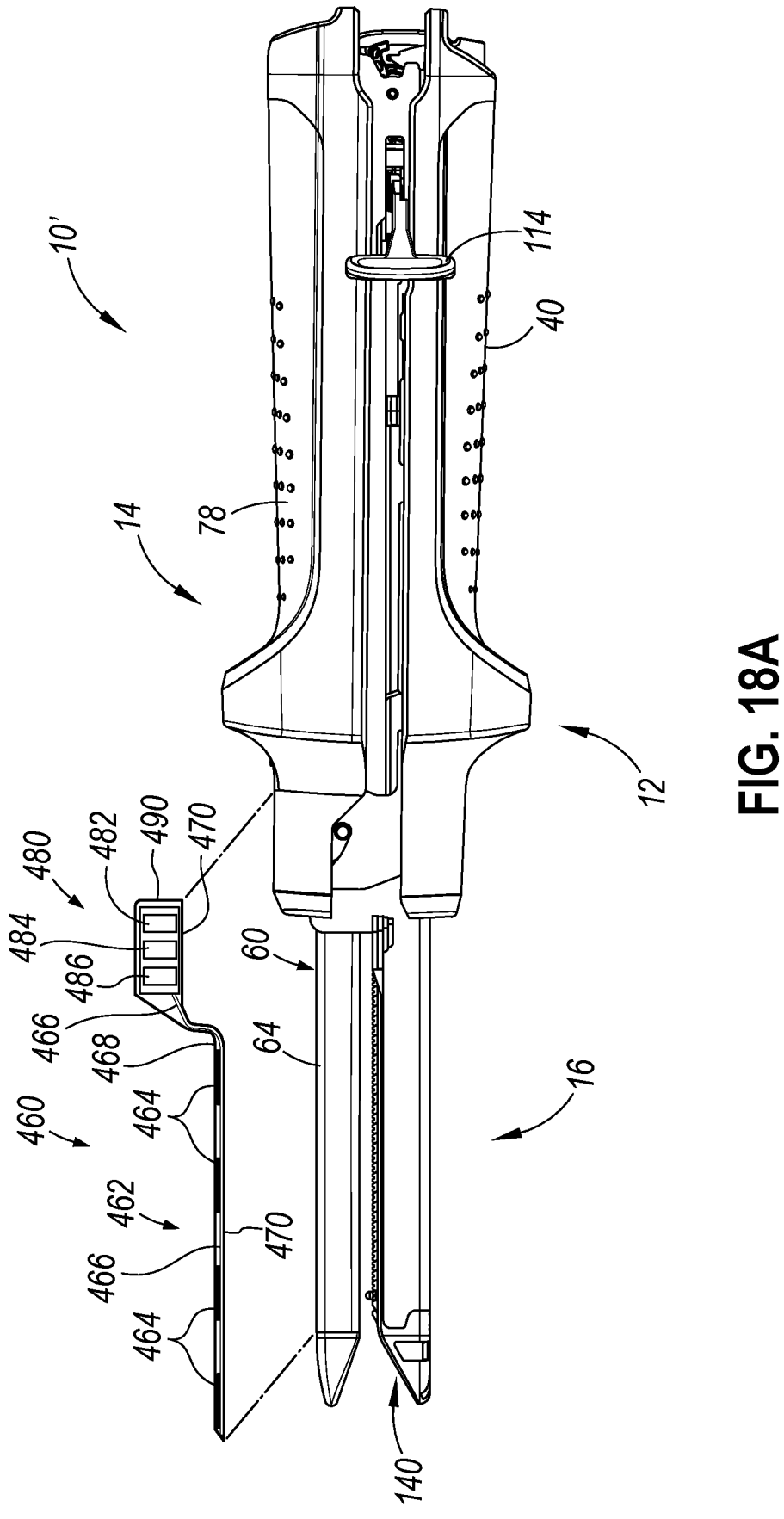
FIG. 18A depicts a side elevational view of the linear surgical stapler of FIG. 1 and an anvil strain measuring assembly detached from each other.
Figure 18B:
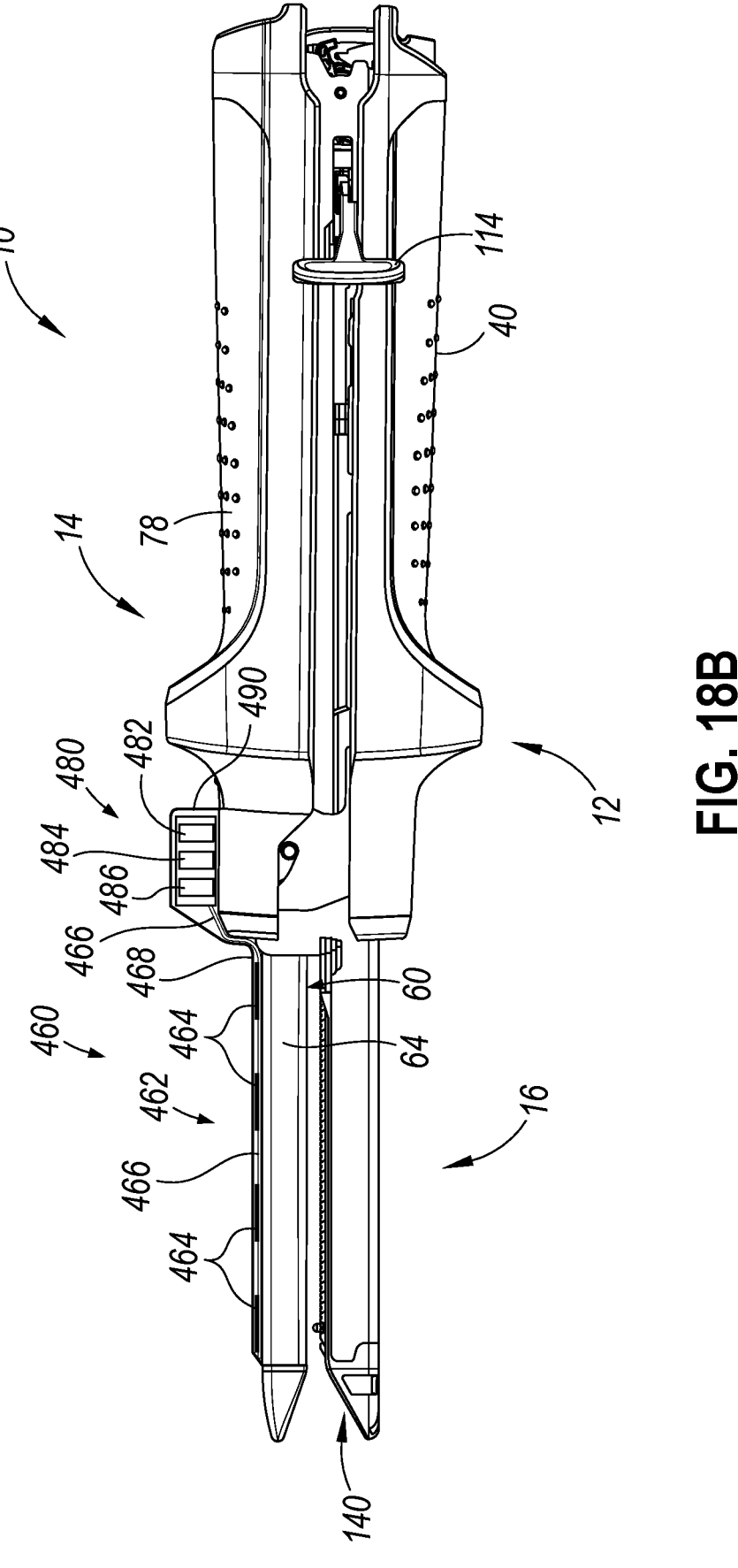
FIG. 18B depicts a side elevation view of the linear surgical stapler of FIG. 1 and the anvil strain measuring assembly of FIG. 18A operatively attached to each other.

FIGS. 16A-16B show an illustrative use of surgical stapler (10) and clamp lever force measuring assembly (360) to clamp tissue, while FIG. 17 shows an illustrative method (1100) of clamp lever force measuring assembly (360) and console (202) determining if a suitable gap distance (d) is present such that the risk of malformed/open fired staples is low; or if an unsuitable gap distance (d) is present such that the risk of malformed/open fired staples is high. First, a user may clamp tissue (1102) between deck (156) of staple cartridge (140) and anvil plate (72) of elongate anvil channel (60) by utilizing clamp lever (40) in accordance with the teachings herein. In such an instances, anvil latching pin (68) is driven into the clamped configuration via suitable engagement with curved slot (50) defined by opposed jaws (48) of clamp lever (40). As mentioned above, generally, the thicker clamped tissue results in both larger clamping forces (and resulting larger strains on anvil channel (60)) and larger gap distance (d) between anvil plate (72) and deck (156).

While tissue is suitably clamped, sensor (380) of sensor unit (362) measures (1104) the resulting force of clamp lever (40) and/or the angle between clamp lever (40) and proximal frame portion (18). The measured (1104) force and/or angle is communicated to electronic module (365) such that control unit (366) receives the measurement. Control unit (366) may then send the measurement to wireless transmitter (368), which in turn wirelessly communicates (1106) the measurement to surgeon's console (202). Next, console (202) may process the received measurement by comparing (1108, 1112) the measured strain from sensor unit (362) to a predetermined limit stored on console (202).

In this example, console (202) determines if the measured parameter is over the predetermined limit (1108) and/or determines if the measured parameter is within (e.g., below) the predetermined limit (1112). If the measured parameter is above the predetermined limit, console (202) communicates (1110) to the user that a high risk of malformed and/or open staples exists if the user were to actuate firing assembly (110) with the current clamping status. Similarly, if the measured parameter is outside the predetermined limit, console (202) communicates (1110) to the user that a high risk of malformed and/or open staples exists if firing assembly (110) were to be distally actuated (e.g., fired) with the current clamping status. However, if the measured parameter is under the predetermined limit and/or within the predetermined range, console (202) communicates (1114) to the user that a low risk of malformed and/or open staples exits firing assembly (110) were to be distally actuated (e.g., fired) with the current clamping status.

In this illustrative use, it should be understood that control unit (366) may have sent item specific predetermined limit (s) determined and stored on control unit (366) during assembly of a specific item to surgeon's console (202). In some instances, surgeon's console (202) and/or control unit (366) may already have generic predetermined limits stored associated with a make and model of a surgical stapler. While console (202) made the comparison (1108, 1112) in the current example, it should be understood that in some instances, control unit (366) may make the comparisons and communicate the results to console (202) for display to a user.

FIGS. 18A-20B show an illustrative anvil strain measuring assembly (460) configured to couple to linear surgical stapler (10) in order to form a modified stapler (10') for illustrative use with surgeon's console (202). Once assembled onto linear surgical stapler (10), anvil strain measuring assembly (460) is configured to measure strain along the length of distal jaw portion (64). The measured strain is indicative of a closure force profile along the length distal jaw portion (64); which may also be indicative of the gap distance (d) between deck (156) and anvil plate (72). Further, anvil strain measuring assembly (460) is configured to communicate the measurements to surgeon's console (202) in order to display information related to such measurements to a user (e.g., level of risk of malformed/open staples forming).

Anvil strain measuring assembly (460) includes a distal strain gauge portion (462) and a proximal electronic unit (480) stored within a housing (490). Distal strain gauge portion (462), proximal electronic unit (480), and housing (490) are attached to each other to form a unitary device. Proximal electronic unit (480) is substantially similar to electronic unit (265, 265) described above. Therefore, electronic unit (480) includes a control unit (482), a wireless transmitter (484), and a battery (486); which are substantially similar to control unit (266, 366), wireless transmitter (268, 368), and battery (270, 370) described above, respectively.

Distal strain gauge portion (462) includes a plurality of strain gauges (464), a plurality of flexible circuits (466), an external coating (468), and an adhesive (470). External coating covers at least an outer surface of strain gauges (464) while flexible circuits (466) extend along external coating (468). Flexible circuits (466) are coupled to a respective strain gauge (464) and extend into communication with proximal electronic unit (480). Flexible circuit (466) provides communication between a respective strain gauge (464) and electronic unit (480), thereby allowing electronic unit (480) to communicate measurements received from strain gauges (464) and transmit suitable information related to such received measurements to surgeon's console (202).

Figure 19:
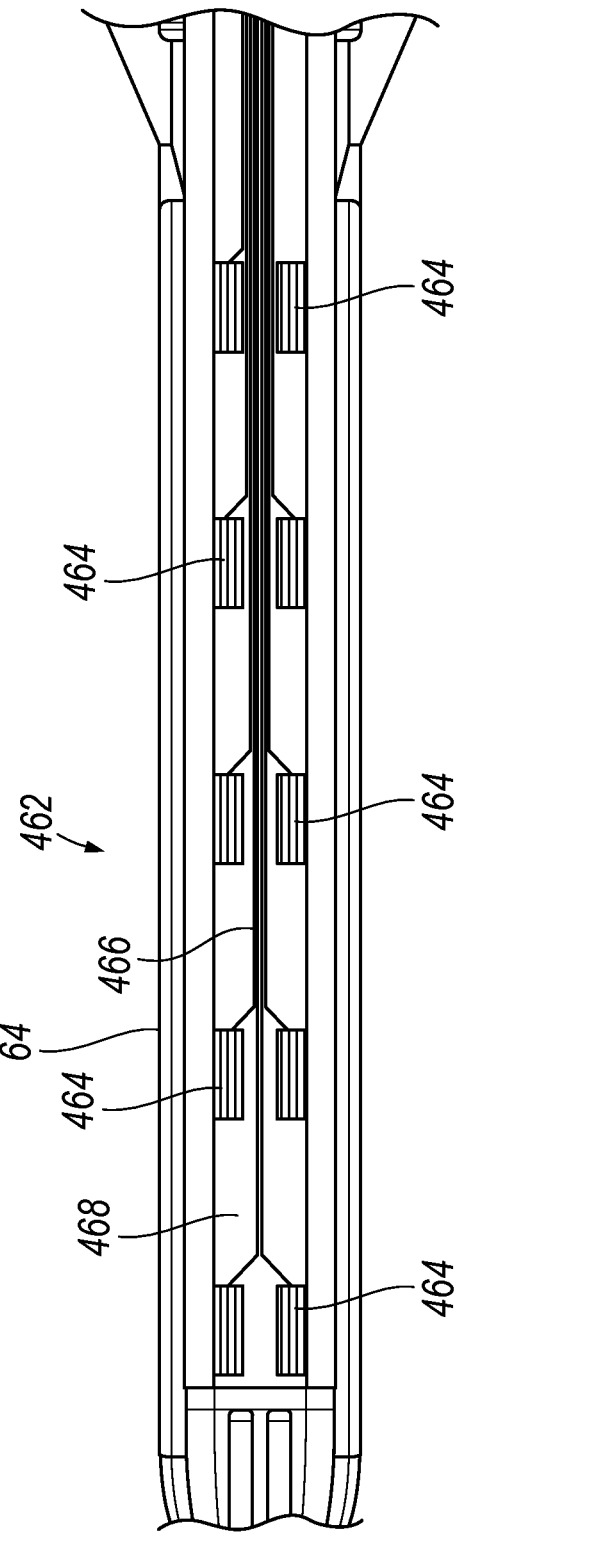
FIG. 19 depicts a top plan view of a portion of the anvil strain measuring assembly of FIG. 18A operatively attached to the anvil half of the linear surgical stapler of FIG. 1.

When anvil strain measuring assembly (460) is suitably coupled to linear stapler (10), thereby forming modified linear stapler (10'), strain gauges (464) are suitably attached to corresponding portions of distal jaw portion (64) such that an array of strain gauges (464) extend along the length of distal jaw portion (64) and on corresponding lateral sides of distal jaw portion (64), as shown in FIG. 19. When suitably coupled, strain gauges (464) are configured to measure the strain within corresponding portions of distal jaw portion (64). Such measured strain is indicative of the closure force imparted on distal jaw portion (64) while clamping tissue in accordance with the teachings herein.

External coating (468) extends along the length of strain gauge portion (262) and connects with housing (490) such that housing (490) and coating (468) form an exterior surface. As mentioned above, a bottom side of distal strain gauge portion (462) includes an adhesive (470), which may come in the form of an adhesive layer. Adhesive (470) may also extend on the underside of housing (490) in order to selectively couple housing (490) with adjacent portions of shroud (78). Therefore, as shown between FIGS. 18A-18B, an underside of housing (490) is placed on top of a proximal portion of shroud (78); while an underside of strain gauge portion (62) is placed on the top surface of distal jaw portion (64) such that adhesive at least affixes (at least temporarily for illustrative use) anvil strain measuring assembly (460) to respective portions of distal jaw portion (64) and shroud (78). Once anvil strain measuring assembly (460) is suitably attached to linear stapler (10), thereby forming modified linear stapler (10'), strain gauges (462) are suitably engaged with distal jaw portion (64) in order to measure the strain within corresponding portions of jaw portion (64) while clamping tissue in accordance with the description herein.

While the current illustrated example shows anvil strain measuring assembly (460) configured to selectively attach to components of linear stapler (10) in order to form modified linear stapler (10'), it should be understood that clamp force measuring assembly (460) may be integrated with surgical stapler (10') such that no additional assembly after manufacturing is required (i.e., measuring force assembly (460) is manufactured as an integral component of stapler (10'). In such instances, housing (490) may be an integrated component of shroud (78) or other suitable components of linear stapler (10) as would be apparent to one skilled in the art in view of the teachings herein.

As mentioned above, electronic unit (480) is configured to transmit measurements received from strain gauges (464) to surgeon's console (202). Since multiple strain gauges (464) are located along the length of distal jaw portion (64), as well as on lateral sides of distal jaw portion (64), console (202) may use such data to display clamping loads at different locations of distal jaw portion (64). For example, surgeon's console (202) may receive strain measurement from strain gauges (464) during illustrative use (e.g., while stapler (10') clamps tissue), interpret the measurements as clamping loads imparted on distal jaw portion (64), and visually display the clamping loads on a digital representation (410) (see FIG. 21) of anvil plate (72).

Figure 20A:
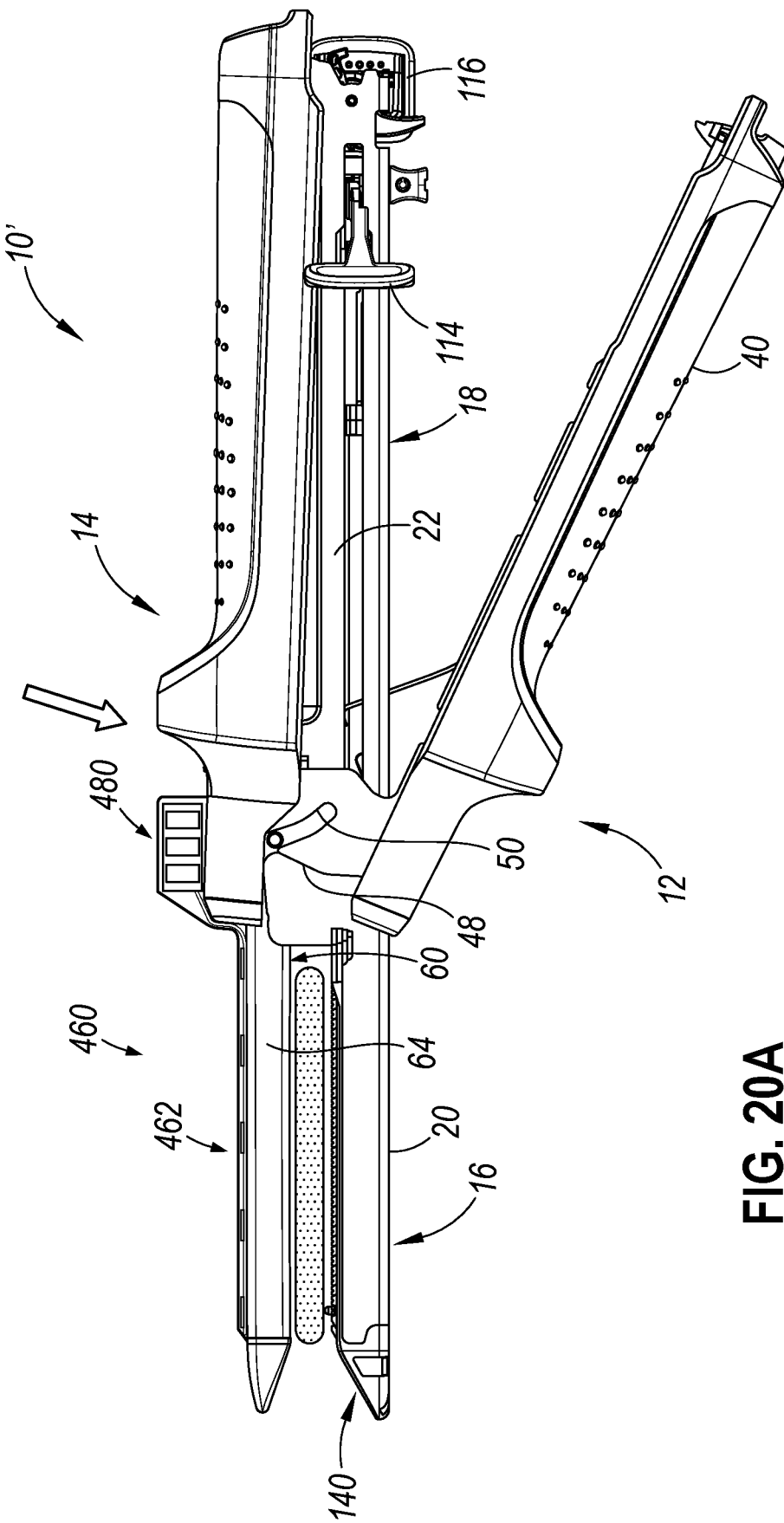
FIG. 20A depicts a side elevational view of the linear surgical stapler of FIG. 1 operatively attached to the anvil strain measuring assembly of FIG. 18A, showing distal portions of the stapler halves having been approximated so that a distal pin of the anvil half is received by clamp lever jaws of the cartridge half.
Figure 20B:
FIG. 20B depicts a side elevational view of the linear surgical stapler of FIG. 1 operatively attached to the anvil strain measuring assembly of FIG. 18A, showing closure of the clamp lever to fully clamp the stapler halves together.
Figure 21:
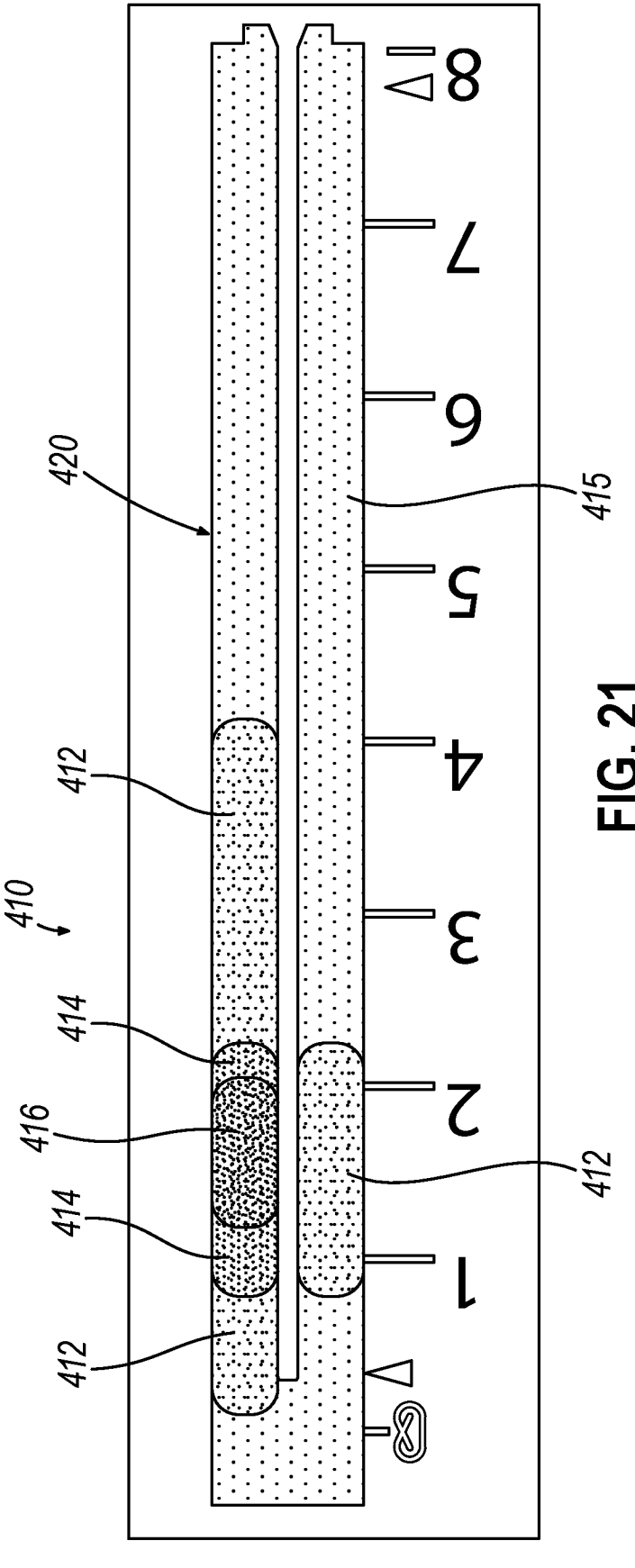
FIG. 21 depicts a graphical display of a visual display of tissue loading of the linear surgical stapler of FIG. 1 while operatively attached to the anvil strain measuring assembly of FIG. 18A.
Figure 22:
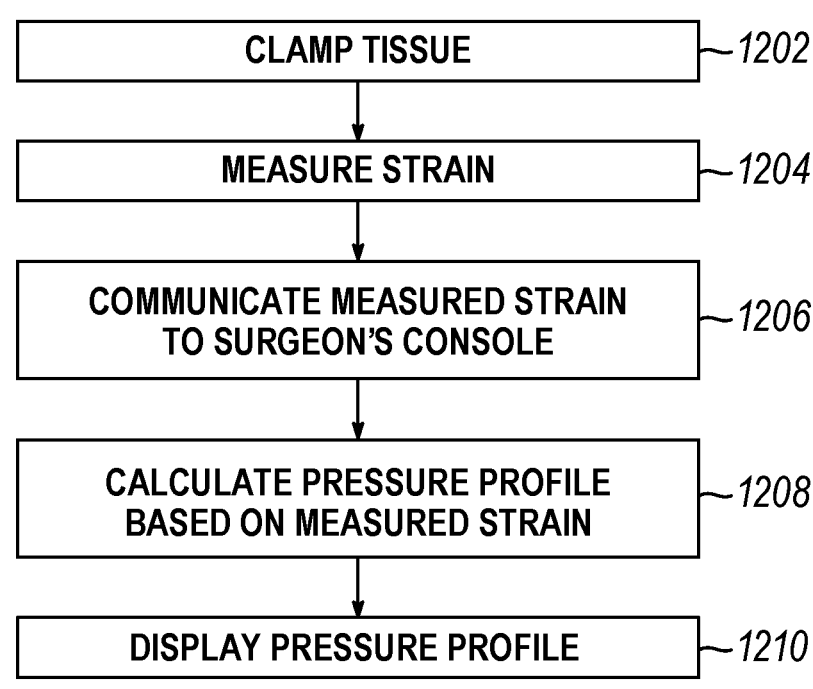
FIG. 22 depicts a flowchart of an exemplary method of use of a linear surgical stapler having an anvil strain measuring assembly.

FIGS. 20A-20B show an exemplary use of modified linear stapler (10'), while FIG. 22 shows an exemplary method (1200) of using modified linear stapler (10') and surgeon's console (202) to visually display a graphical representation of active clamping loads on an anvil plate (72) as illustrated in FIG. 21.

First, prior to illustrative use, electronic unit (480) may establish suitable communication with console (202) via wireless transmitter (484). During illustrative use, surgical stapler (10') may be used to clamp tissue (1202) in accordance with the description herein, as shown in FIG. 20A-20B. Strain gauges (464) measure (1204) a strain value at respective locations on distal anvil jaw (64). Measured (1204) strain is communicated from strain gauges (464) to electronic unit (480) via flexible circuits (466), and electronic unit (480) then communicate (1206) the measured strain to surgeon's console (202). Surgeon's console (202) then calculates (1208) a pressure profile based on the measured (1204) strain and displays (1211) a pressure profile of anvil plate (72) to the surgeon via display of console (202).

As mentioned above, FIG. 21 shows an illustrative digital representation (410) of a pressure profile (420) on anvil plate (72) clamping tissue. The current visual digital representation (410) shows a pressure profile (410) of acceptable clamping loads (415) along a substantial length of anvil plate (72), with relatively higher clamping loads (420) along a more distal portion of anvil plate (72). Additionally, one lateral side of anvil plate (72) is shown to be experienced higher than desirable clamping loads (414) and unacceptable clamping loads (416) on one lateral side of anvil plate (72) at a distal end. This may be indicative that stapler (10') is grasping either too thick of tissue or foreign objects that are not intended to be clamped, such as previously fired staples, etc. Therefore, a user may view the illustrative digital representation (410) shown in FIG. 21 and try to re-clamp tissue in order to achieve a more desirable pressure profile (420).

Console (202) may additionally or alternatively display any other suitable information or notifications as would be apparent to one skilled in the art in view of the teachings herein. For example, console (202) may display recommendation to fire stapler (10') or recommending to re-clamp tissue; displaying the chances of successful staple formation in light of the current pressure profile, etc. Console (202) may alert a user in light of such calculations.

Control unit (482) may include suitable calibration information related to strain gauges (464) for a specific surgical stapler (10) (e.g., when anvil strain measuring assembly (60) is integrated into surgical stapler); or may contain generic calibration information for strain gauges (464) in relation to a specific make or model of surgical stapler (10). In some instances, surgeons console (202) may contain the generic calibration information for the specific make or model of surgical stapler (10).

Figure 23:
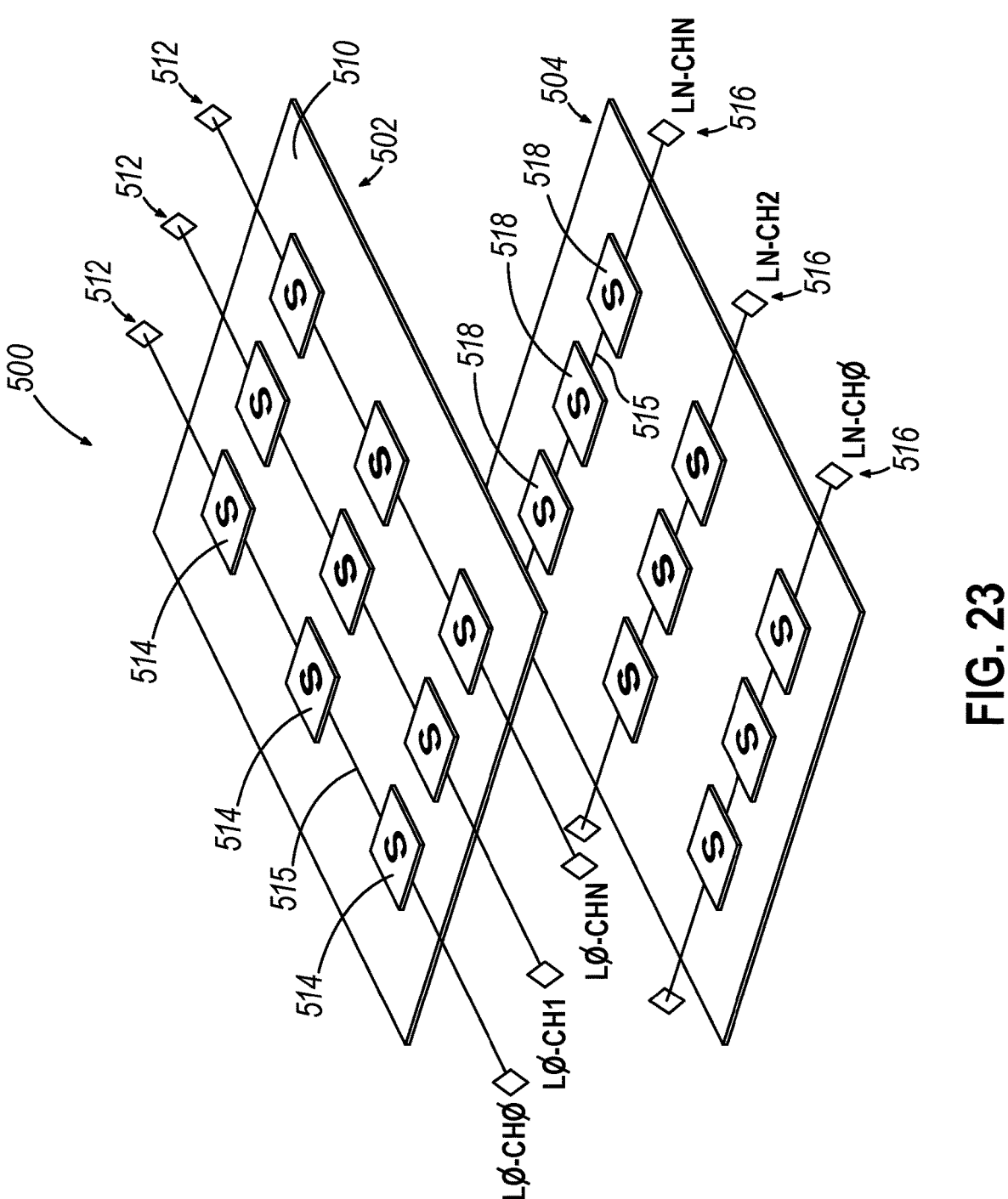
FIG. 23 depicts an exploded perspective view of an illustrative strain measuring sensor.

FIG. 23 shows an illustrative piezoelectric sensor assembly (500). Sensor assembly (500) includes a first layer (502) and a second layer (504). Each layer (502, 504) includes a base player (510) and a plurality of arrays consisting of respective channels channels (512, 516) each having a respective array of piezoelectric sensors (514, 518) connected to each other in a series via wiring (515). Arrays of channels (512, 516) are layered so that their channels (512, 516) are orthogonal relative to each other and sensor (514, 518) aligned as shown in FIG. 23. Each channel (512, 516) is provided a current source. The voltage drop over each channel (512, 516) determine the respective sensors (514, 518) resistive properties. Force location can be identified on two axis by channel measurements. Aligning the location of sensors with staple pressure points can help identify successful and unsuccessful staple fires. These sensors could be placed side staple cartridge or as an added layers. Sensor arrays could also be used to determine variations in tissue thickness in areas of interest. These measurements could inform the user on potential quality of activation or stapling.

Figure 24A:
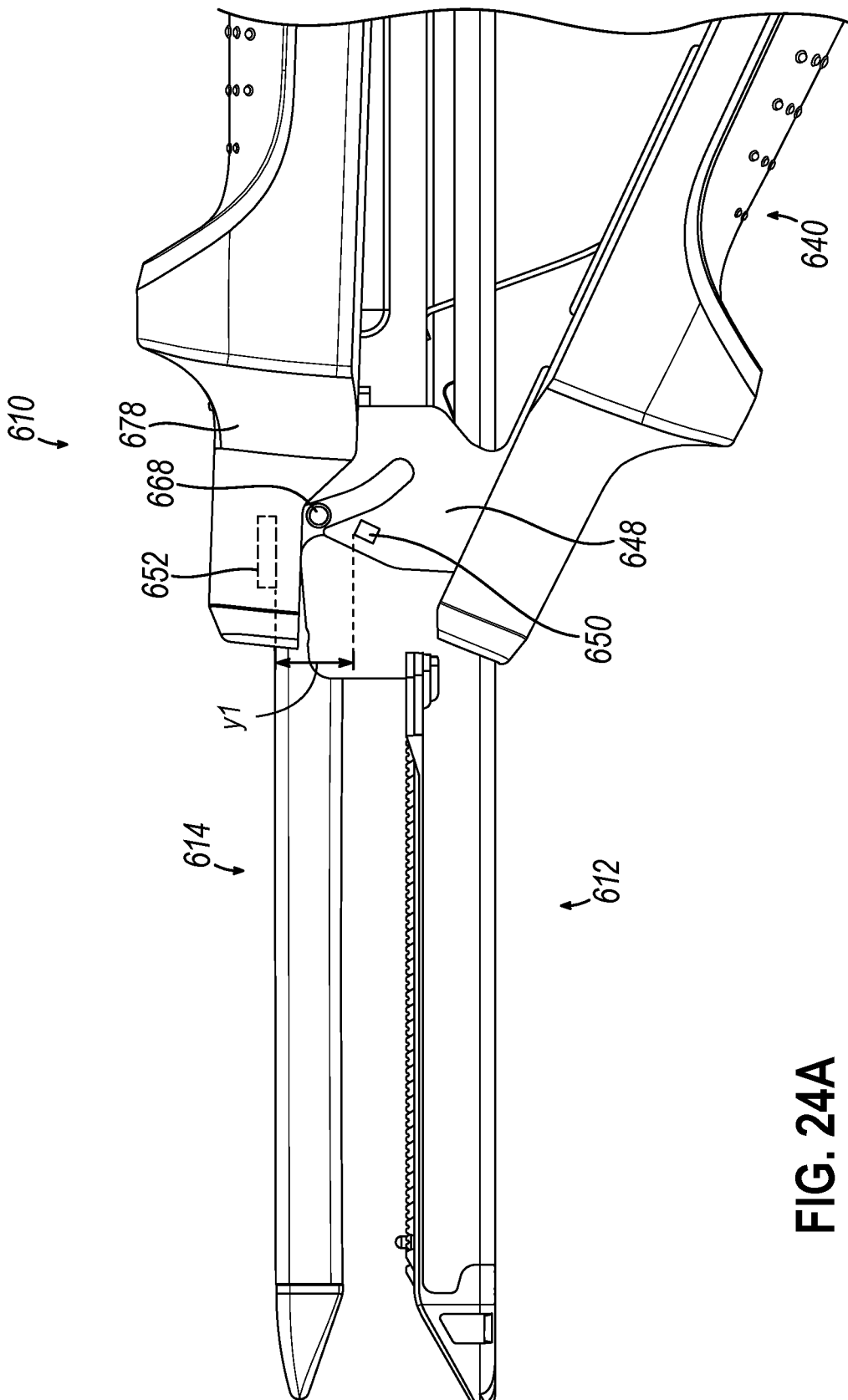
FIG. 24A depicts a side elevational view of a linear surgical stapler, showing distal portions of the stapler halves having been approximated so that a distal pin of the anvil half is received by clamp lever jaws of the cartridge half.
Figure 24B:
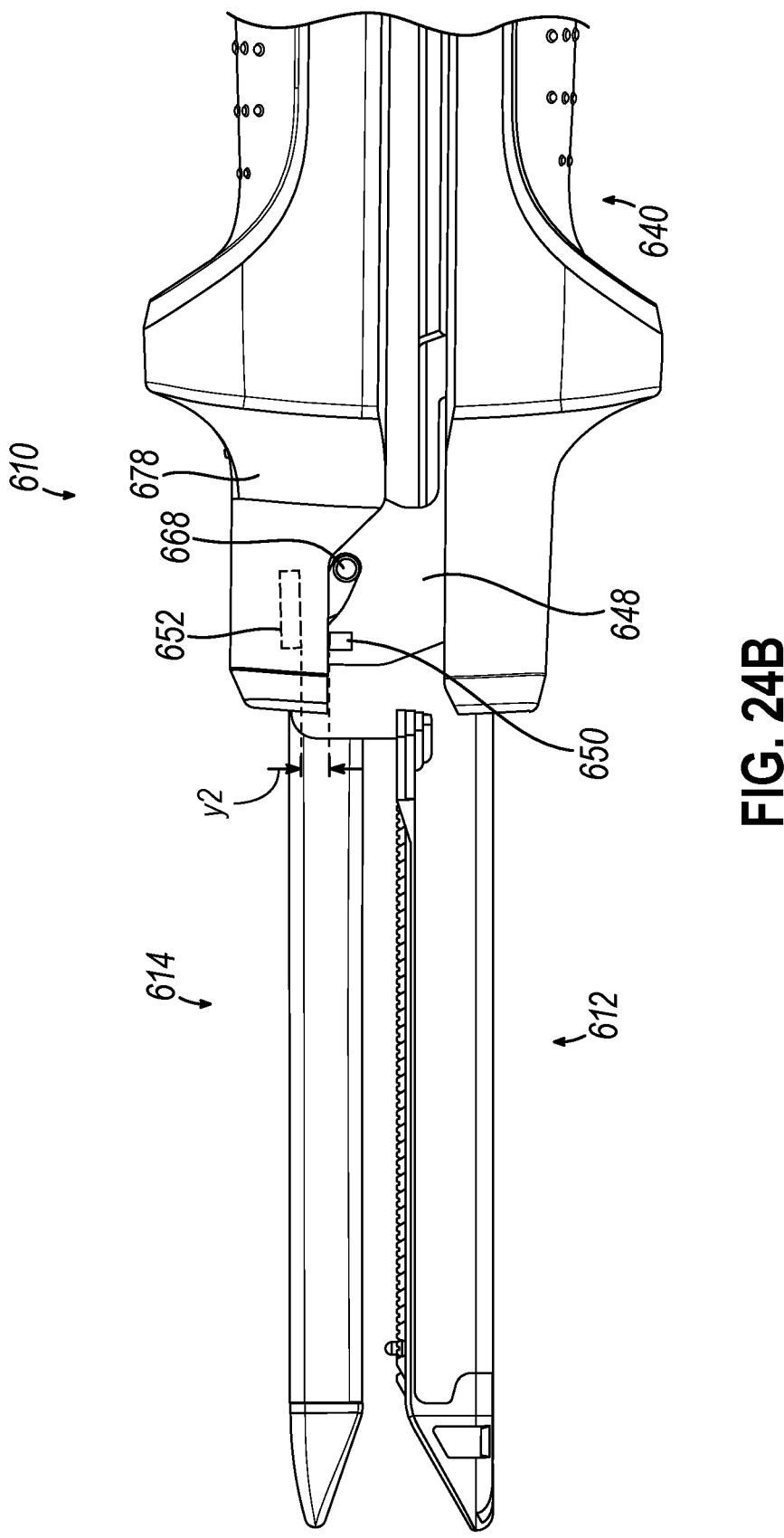
FIG. 24B depicts a side elevational view of the linear surgical stapler of FIG. 24A, showing closure of the clamp lever to fully clamp the stapler halves together.

FIGS. 24A-24B show an alternative surgical stapler (610) that is substantially similar to surgical stapler (10, 210, 310, 410) described above, with differences elaborated below. Surgical stapler (610) includes a cartridge half (612), an anvil half (614), a clamp lever (640), jaws (648), an anvil pin (668), and a shroud (678); which are substantially similar to cartridge half (12), anvil half (14), clamp lever (40), jaws (48), anvil pin (68), and shroud (678) described above. Surgical stapler (610) also includes a Hall Effect sensor (652) associated with shroud (678) and a magnet (650) associated with jaws (650). Hall effect sensor (652) is in communication with an electronic unit (not shown) which is substantially similar to electronic unit (265, 365, 480) described above. Therefore, measurements taken by Hall effect senor (652) may be communicated to surgeon's console (202) via electronic unit (not shown).

Hall effect sensor (652) may sense the position of magnet (650) as clamp lever (640) actuates toward anvil half (614) in accordance with the description herein. The position of magnet (650) relative to hall effect sensor (652) is indicative of the gap distance (d) between distal portion of cartridge half (612) and anvil half (614). Therefore, console (202) may use the measurements from hall effect sensor (652) to determine if a suitable gap distance (d) is present before actuating firing assembly of stapler (610). Console (202) may alert a user of an acceptable or unacceptable gap distance (d) based on the measurement of hall effect sensor (652).

As mentioned above, item specific predetermined limit(s) (e.g., predetermined stain limits) may be utilized in order to determine whether or not the risk of malformed or open staples is unacceptably high while clamping tissue in accordance with the teachings herein. Such item specific predetermined limit(s) may be determined with a suitable calibration process. Such a calibration process may include clamping a load cell with surgical stapler (10, 210, 310, 410, 610) with an acceptable gap distance and/or force, measuring the suitable parameter with sensor (262, 362, 464, 652), and using the measured suitable parameter while clamping a load cell with an acceptable gap distance and/or force to calculate the specific predetermined limit(s).

II. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a first elongate member having a distal portion configured to present a first stapling surface; (b) a second elongate member having a distal portion configured to present a second stapling surface, wherein the first and second elongate members are configured to releasably couple together to enable the first and second stapling surfaces to cooperate to clamp and staple tissue with a plurality of staples; (c) a clamp member, wherein the clamp member is movable relative to the first and second elongate members from a first position to a second position to approximate the first and second stapling surfaces for clamping tissue; (d) a latch member configured to transition from an unlatched state to a latched state to releasably retain the clamp member in the second position; (e) a firing assembly, wherein the firing assembly is actuatable from a home position to fire the staples into the clamped tissue; and (f) a clamp force measuring assembly, wherein the clamp force measuring assembly is configured to: (i) measure a parameter associated with a clamping force imparted on the first and second stapling surfaces clamping tissue, and (ii) process and communicate the measured parameter to be compared with a predetermined limit associated with successful staple formation.

Example 2

The apparatus of Example 1, wherein the clamp force measuring assembly comprises a strain gauge attached to the latch member, wherein the measured parameter comprises a strain measurement.

Example 3

The apparatus of Example 2, wherein the latch member comprises a jaw defining a slot, wherein the strain gauge is directly adjacent to a portion of the jaw defining the slot.

Example 4

The apparatus of Example 3, wherein the clamp force measuring assembly comprises a electronic unit in communication with the strain gauge, wherein the electronic unit is configured to receive the measured strain from the strain gauge.

Example 5

The apparatus of any one or more of Examples 1 through 4, wherein the electronic unit comprises a battery configured to power the strain gauge.

Example 6

The apparatus of any one or more of Examples 1 through 5, wherein the electronic unit comprises a wireless transmitter configured to communicate the processed measured parameter to a surgeon's console.

Example 7

The apparatus of Example 1, wherein the clamp force measuring assembly is configured to selectively attach to the latch member.

Example 8

The apparatus of Example 1 or 7, wherein the clamp force measuring assembly comprises a sleeve housing an electronic unit.

Example 9

The apparatus of any one or more of Examples 7 through 8, wherein the clamp force measuring assembly comprises a first leg and a second leg, wherein the parameter comprises a measured angle between the first leg and the second leg.

Example 10

The apparatus of Example 8, wherein the clamp force measuring assembly comprises a first leg and a second leg, wherein the parameter comprises a force imparted on either the first leg or the second leg.

Example 11

The apparatus of claim 1, wherein the clamp force measuring assembly comprises a strain gauge assembly attached to a top surface of the first elongate member.

Example 12

The apparatus of Example 11, wherein the clamp force measuring assembly is further configured to measure a plurality of strain gauges along the top surface of the first elongate member.

Example 13

The apparatus of Example 11, wherein the plurality of strain gauges are configured to selectively attach to the top surface of the first elongate member.

Example 14

The apparatus of any one or more of Examples 1 through 13, wherein the clamp force measuring assembly comprises an electronic unit.

Example 15

The apparatus of Example 14, wherein the electronic unit comprises a control unit, a wireless transmitter, and a battery, wherein the battery is configured to electrically power the control unit and the wireless transmitter.

Example 16

An apparatus comprising: (a) a first elongate member having a distal portion configured to present a first stapling surface; (b) a second elongate member having a distal portion configured to present a second stapling surface, wherein the first and second elongate members are config-ured to releasably couple together at their proximal ends to enable the first and second stapling surfaces to cooperate to clamp and staple tissue with a plurality of staples; (c) a clamp member, wherein the clamp member is movable relative to the first and second elongate members from an open position to a closed position to approximate the first and second stapling surfaces for clamping tissue; and (d) a strain measurement assembly configured to measure a strain value associated with either the first elongate member or the clamp member, wherein the strain measurement assembly is configured to communicate the measured strain to a console configured generate a signal indicative of whether a gap distance between the first and second stapling surfaces is within a predetermined range.

Example 17

The apparatus of Example 16, wherein the strain measur-ing assembly comprises a control unit configured to generate the signal.

Example 18

The apparatus of Example 17, wherein the strain measur-ing assembly comprises a battery configured to power the control unit.

Example 19

The apparatus of any one or more of Examples 16 through 18, wherein the first elongate member comprises an anvil surface defining a plurality of staple forming pockets.

Example 20

A method of determining whether a gap distance between a first and second stapling surface is within a predetermined range, the method comprising: (a) measuring a strain value on a first elongate member while the first elongate member and a second elongated member cooperate to clamp tissue; (b) communicating the measured strain value to a console; and (c) generating a pressure profile on the first stapling surface using the measured strain value.

III. Miscellaneous

It should be understood that any one or more of the teachings, expressions, embodiments, examples, etc. described herein may be combined with any one or more of the other teachings, expressions, embodiments, examples, etc. that are described herein. The above-described teach-ings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more teachings disclosed herein may be combined with any one or more teachings disclosed in U.S. Pat. No. 10,631,866, entitled "Release Mechanism for Linear Surgical Stapler," issued Apr. 28, 2020; U.S. Pat. No. 10,667,818, entitled "Lockout Assembly for Linear Surgical Stapler," issued Jun. 2, 2020; U.S. Pat. No. 10,932,781, entitled "Features to Align and Close Linear Surgical Sta-pler," issued Mar. 2, 2021; U.S. Pat. No. 10,898,197, entitled "Releasable Coupling Features for Proximal Portions of Linear Surgical Stapler," issued Jan. 26, 2021; U.S. Pat. No. 10,874,398, entitled "Firing Lever Assembly for Linear Surgical Stapler," issued Dec. 29, 2020; U.S. Pat. No. 10,687,819, entitled "Clamping Mechanism for Linear Sur-gical Stapler," issued Jun. 23, 2020; U.S. Pat. No. 10,898, 187, entitled "Firing System for Linear Surgical Stapler," issued Jan. 26, 2021; U.S. Pat. No. 11,033,266, entitled "Decoupling Mechanism for Linear Surgical Stapler, issued Jun. 15, 2021; U.S. Pat. No. 11,045,193, entitled "Anvil Assembly for Linear Surgical Stapler," issued Jun. 29, 2021; U.S. Pat. No. 10,905,419, entitled "Closure Assembly for Linear Surgical Stapler," issued Feb. 2, 2021; U.S. Pat. No. 11,278,285, entitled "Clamping Assembly for Linear Surgi-cal Stapler," issued Mar. 22, 2022; U.S. Pat. No. 11,229,433, entitled "Linear Surgical Stapler," issued Jan. 25, 2022; U.S. Pub. No. 2022/0142641, entitled "System and Method for Forming Pockets in Anvil of Surgical Stapler," published May 12, 2022, issued as U.S. Pat. No. 12,016,555 on Jun. 25, 2024; U.S. Pat. No. 11,224,425, entitled "Surgical Linear Cutter Wishbone Separation Mechanism with Detent," issued Jan. 18, 2022; U.S. Pat. No. 11,219,454, entitled "Pin Trap Mechanism for Surgical Linear Cutter," issued Jan. 11, 2022; U.S. Pub. No. 2021/0369272, entitled "Separation Mechanism for Surgical Linear Cutter," published Dec. 2, 2021, issued as U.S. Pat. No. 11,399,827 on Aug. 2, 2022; U.S. patent application Ser. No. 17/489,879, entitled "Lock-out Feature for Linear Surgical Stapler Cartridge," filed Sep. 30, 2021, Issued as U.S. Pat. No. 11,937,812 on Mar. 26, 2024; U.S. patent application Ser. No. 29/842,580, entitled "Staple Cartridge for Linear Surgical Stapler," filed Jun. 16, 2022; and/or U.S. patent application Ser. No. 29/842,581, entitled "Linear Surgical Stapler," filed Jun. 16, 2022, issued as U.S. Design Pat. No. D1,067,431 on Mar. 18, 2026. The disclosure of each of these references is incorporated by reference herein, in its entirety.

Furthermore, any one or more of the teachings herein may be combined with any one or more of the teachings disclosed in U.S. patent application Ser. No. 18/500,297, entitled "Strain and Compression Force Measurement Features for Surgical Stapler," filed Nov. 2, 2023 and published as U.S. Pat. Pub. No. 2025/0143733 on May 8, 2025, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other dis-closure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other dis-closure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a first elongate body having a distal portion configured to present a first stapling surface;
(b) a second elongate body having a distal portion configured to present a second stapling surface, wherein the first and second elongate bodies are configured to releasably couple together to enable the first and second stapling surfaces to cooperate to clamp and staple tissue with a plurality of staples;
(c) a clamp, wherein the clamp is movable relative to the first and second elongate bodies from a first position to a second position to approximate the first and second stapling surfaces for clamping tissue;
(d) a latch configured to transition from an unlatched state to a latched state to releasably retain the clamp in the second position;
(e) a firing assembly, wherein the firing assembly is actuatable from a home position to fire the staples into the clamped tissue; and
(f) a clamp force measuring assembly, wherein the clamp force measuring assembly is configured to:
(i) measure a parameter associated with a clamping force imparted on the first and second stapling surfaces clamping tissue, and
(ii) process and communicate the measured parameter to be compared with a predetermined limit associated with successful staple formation, wherein the clamp force measuring assembly is configured to selectively attach to the latch.

2. The apparatus of claim 1, wherein the clamp force measuring assembly comprises a strain gauge attached to the latch, wherein the measured parameter comprises a strain measurement.

3. The apparatus of claim 2, wherein the latch comprises a jaw defining a slot, wherein the strain gauge is directly adjacent to a portion of the jaw defining the slot.

4. The apparatus of claim 3, wherein the clamp force measuring assembly comprises an electronic unit in communication with the strain gauge, wherein the electronic unit is configured to receive the measured strain from the strain gauge.

5. The apparatus of claim 4, wherein the electronic unit comprises a battery configured to power the strain gauge.

6. The apparatus of claim 5, wherein the electronic unit comprises a wireless transmitter configured to communicate the processed measured parameter to a surgeon's console.

7. The apparatus of claim 1, wherein the clamp force measuring assembly comprises a strain gauge assembly attached to a top surface of the first elongate body.

8. The apparatus of claim 7, wherein the clamp force measuring assembly is further configured to measure a plurality of strain gauges along the top surface of the first elongate body.

9. The apparatus of claim 7, wherein the plurality of strain gauges are configured to selectively attach to the top surface of the first elongate body.

10. The apparatus of claim 1, wherein the clamp force measuring assembly comprises an electronic unit.

11. The apparatus of claim 10, wherein the electronic unit comprises a control unit, a wireless transmitter, and a battery, wherein the battery is configured to electrically power the control unit and the wireless transmitter.

12. The apparatus of claim 1, wherein the clamp force measuring assembly comprises a sleeve housing an electronic unit.

13. The apparatus of claim 12, wherein the clamp force measuring assembly comprise a first leg and a second leg, wherein the parameter comprises a measured angle between the first leg and the second leg.

14. The apparatus of claim 12, wherein the clamp force measuring assembly comprises a first leg and a second leg, wherein the parameter comprises a force imparted on either the first leg or the second leg.

15. An apparatus comprising:
(a) a first elongate body having a distal portion configured to present a first stapling surface;
(b) a second elongate body having a distal portion configured to present a second stapling surface, wherein the first and second elongate bodies are configured to releasably couple together to enable the first and second stapling surfaces to cooperate to clamp and staple tissue with a plurality of staples;

(c) a clamp, wherein the clamp is movable relative to the first and second elongate bodies from a first position to a second position to approximate the first and second stapling surfaces for clamping tissue;

(d) a latch configured to transition from an unlatched state to a latched state to releasably retain the clamp in the second position;

(e) a firing assembly, wherein the firing assembly is actuatable from a home position to fire the staples into the clamped tissue; and (f) a clamp force measuring assembly, wherein the clamp force measuring assembly comprises a strain gauge attached to the latch, wherein the measured parameter comprises a strain measurement, wherein the latch comprises a jaw defining a slot, wherein the strain gauge is directly adjacent to a portion of the jaw defining the slot, wherein the clamp force measuring assembly is configured to:

(i) measure a parameter associated with a clamping force imparted on the first and second stapling surfaces clamping tissue, and (ii) process and communicate the measured parameter to be compared with a predetermined limit associated with successful staple formation.

\* \* \* \* \*